(12) United States Patent
Slager et al.

(10) Patent No.: US 9,770,537 B2
(45) Date of Patent: Sep. 26, 2017

(54) SOLVENT METHODS FOR PREPARING CRYSTALLINE MACROLIDE PARTICULATES, COMPOSITIONS, AND ARTICLES CONTAINING PARTICULATES

(71) Applicant: SurModics, Inc., Eden Prairie, MN (US)

(72) Inventors: Joram Slager, Saint Louis Park, MN (US); Aleksey V. Kurdyumov, Lino Lakes, MN (US); Toni M. Heyer, Saint Louis Park, MN (US)

(73) Assignee: SURMODICS, INC., Eden Prairie, MN (US)

( * ) Notice: Subject to any disclaimer, the term of this patent is extended or adjusted under 35 U.S.C. 154(b) by 0 days.

(21) Appl. No.: 14/303,309

(22) Filed: Jun. 12, 2014

(65) Prior Publication Data

US 2015/0017219 A1    Jan. 15, 2015

Related U.S. Application Data

(60) Provisional application No. 61/834,327, filed on Jun. 12, 2013.

(51) Int. Cl.

| | |
|---|---|
| *A61F 2/00* | (2006.01) |
| *A61L 29/16* | (2006.01) |
| *C07D 498/18* | (2006.01) |
| *A61K 9/14* | (2006.01) |
| *A61K 31/436* | (2006.01) |
| *A61K 9/00* | (2006.01) |

(52) U.S. Cl.
CPC ............... *A61L 29/16* (2013.01); *A61K 9/14* (2013.01); *A61K 31/436* (2013.01); *C07D 498/18* (2013.01); *A61K 9/0019* (2013.01); *A61L 2300/416* (2013.01); *Y10T 428/2982* (2015.01)

(58) Field of Classification Search
USPC ........................................................ 424/423
See application file for complete search history.

(56) References Cited

U.S. PATENT DOCUMENTS

| | | | |
|---|---|---|---|
| 7,232,486 | B2 | 6/2007 | Keri et al. |
| 7,842,312 | B2* | 11/2010 | Burgermeister et al. ..... 424/501 |
| 8,048,448 | B2 | 11/2011 | Ludwig et al. |
| 8,337,733 | B2 | 12/2012 | Westedt et al. |
| 2006/0169199 | A1* | 8/2006 | Keri et al. ....................... 117/23 |
| 2007/0128731 | A1* | 6/2007 | Deshmukh et al. ........... 436/147 |
| 2008/0085880 | A1* | 4/2008 | Viswanath et al. ............ 514/183 |
| 2008/0213375 | A1* | 9/2008 | Ray et al. ...................... 424/489 |
| 2009/0246252 | A1 | 10/2009 | Arps et al. |
| 2012/0028908 | A1 | 2/2012 | Viswanath et al. |
| 2013/0035483 | A1 | 2/2013 | Zeng et al. |
| 2014/0336571 | A1 | 11/2014 | Slager et al. |

FOREIGN PATENT DOCUMENTS

| | | |
|---|---|---|
| WO | WO 2008/013416 | 1/2008 |
| WO | WO 2008/014222 | 1/2008 |
| WO | WO 2012/026896 | 3/2012 |

OTHER PUBLICATIONS

Wen (Front. Chem. Eng. China 2007, 1(3): 277-282).*
Murdock (Toxicological Sciences 101(2), 239-253 (2008).*
Hornedo (Journal of Pharmaceutical Sciences, vol. 88, No. 7, Jul. 1999, pp. 651-660).*

* cited by examiner

*Primary Examiner* — Devang Thakor
(74) *Attorney, Agent, or Firm* — Kagan Binder, PLLC

(57) ABSTRACT

The invention provides therapeutic particulates including a macrolide, such as rapamycin, in solid state crystalline form, having a size of 20µm or less, or 10µm or less. The particulates are formed in one method by preparing a composition with a macrolide and first (e.g., xylene) and second (e.g., an alcohol, acetone, or acetonitrile) solvents. In the composition a maximum solubility for the macrolide that is greater than a maximum solubility of the macrolide dissolved in either the first or second solvent individually. The first and second solvents are then evaporated from the composition to provide the macrolide particulates. In another method, the particulates can be formed by a method including sonication and stirring/evaporation steps, and the particulates can be obtained from a supersaturated solution, formed during the process. Particulates display desirable low polydispersity, and can be used in therapeutic compositions, or can be associated with an implantable or insertable medical device for the treatment of a subject.

23 Claims, 21 Drawing Sheets

Zotarolimus

Everolimus

Sirolimus / Rapamycin

Temsirolimus

Pimecrolimus

Tacrolimus

Ridaforolimus / Deforolimus

US 9,770,537 B2

SOLVENT METHODS FOR PREPARING CRYSTALLINE MACROLIDE PARTICULATES, COMPOSITIONS, AND ARTICLES CONTAINING PARTICULATES

CROSS-REFERENCE TO RELATED APPLICATION

The present non-provisional application claims the benefit of commonly owned provisional Application having Ser. No. 61/834,327, filed on Jun. 12, 2013, entitled MACROLIDE PARTICULATES, METHODS FOR PREPARATION, AND MEDICAL DEVICES INCLUDING SUCH, which application is incorporated herein by reference in its entirety.

FIELD

The invention relates to a macrolide particulates including solid state crystallinity, and methods for their formation. The invention also relates to compositions that include the macrolide particulates and medical devices that are implanted or inserted in the body and associated with the macrolide particulates. The invention also relates to medical treatment methods using the composition and devices.

BACKGROUND

Therapeutic agents can be introduced into a subject by several different routes. Most commonly, therapeutic agents are orally administered because it is a convenient, safe, and cost effective way to make the agent systemically available to the body. However, in many cases, it is desired to deliver therapeutic agent using a route other than oral administration, such as by injection or through use of an insertable or implantable medical device.

Some preparations of therapeutic agent are liquid formulations in which the therapeutic agent is dissolved in an aqueous injection composition and then injected into a subject to provide a therapeutic effect. Other preparations of therapeutic agent can be associated with and released from an insertable or implantable medical device. For example, polymeric coatings for medical devices that include therapeutic agent have been used for the delivery of the therapeutic agent from the coating to a target tissue. In many cases, such coatings are prepared by dissolving the therapeutic agent and polymeric material in a common solvent and applying the composition to a device surface to form a coating. However, technical challenges associated with polymer chemistry, compatibility of the therapeutic agent with the polymer system, and release of the therapeutic agent from the coating following implantation make the preparation of drug-releasing coated devices very challenging.

For example, non-antibiotic macrolides such as rapamycin have been used for the treatment or prevention of various medical disorders. Rapamycin has been used to prevent or minimize tissue response associated with inflammation, fibrosis, and thrombosis, which may be associated with medical device insertion or implantation.

Commerically available rapamycin powder can be crushed or ground for micronization, but particulates that are formed can be substantially heterogenous in size and shape, and this technique can also be detrimental to activity, as well as crystalline morphology. In some preparations, rapamycin can be present in a solid composition in amorphous form, but it has been found that the solid amorphous form will dissolve much faster than a crystalline form and these preparations may be less useful for longer term treatments. There are challenges associated with the preparation of rapamycin particulates of desirable shapes and sizes where particulate includes rapamycin in crystalline form.

SUMMARY

The present invention is directed to macrolide particulates with macrolide in crystalline form in the particulate, methods for their preparation, therapeutic compositions that include the particulates, and also implantable and insertable medical devices that can be associated with the particulates and capable of releasing the macrolide therapeutic in the body. The invention is also directed to use of macrolide particulates for the treatment of a medical condition in a subject, in which the macrolide therapeutic provides a therapeutic effect to a subject, preventively, or for active treatment of a medical condition.

The current disclosure shows the preparation of macrolide particulates having sizes of about 10 µm or less and low polydispersion, wherein the particulate includes macrolide in a crystalline solid state form. The crystallinity and size characteristics of the macrolide particulates are valuable for preparing injectable formulations and implantable or insertable medical devices designed to deliver macrolide in the body. The inventive method of the current disclosure overcomes challenges in the art of preparing macrolide particulates, such as rapamycin particulates including rapamycin in crystalline solid state form, wherein the particulates also have desirable size and shape features.

Macrolide in a crystalline solid state can be useful for prolonging the availability of the macrolide after the particulates are introduced in the body. As opposed to an amorphous solid state, particulates with macrolide in a crystalline solid state can have a substantially longer dissolution rate in the body. Therefore, the macrolide particulates of the present disclosure can be used in various treatment regimens where it is desired to provide macrolide at a treatment site over a wider therapeutic window. In some modes of treatment, the macrolide particulates can be used in a composition or associated with an implantable medical article so the macrolide exhibits a sustained-release profile in the body. The sustained-release profile can allow the macrolide to be available over a longer and more therapeutically useful time period for treatment of medical conditions that indicate a longer course of treatment.

A first embodiment (e.g., method I) of the disclosure is directed to a method for preparing macrolide particulates having a mean size of 10 µm or less, wherein the particulate includes macrolide in crystalline form. This method comprises steps of: (a) dissolving and/or dispersing macrolide in a liquid to form a composition; (b) forming a supersaturated composition; (c) providing sonication in the composition; (d) mechanically stirring and evaporating the composition; (e) ceasing mechanical stirring prior to complete evaporation of the solvent from the composition; and (f) after step (e), removing remaining solvent from the composition to provide the macrolide particulates.

A second embodiment (e.g., method II) of the disclosure is directed to a method for preparing macrolide particulates having a mean size of 20 µm or less, wherein the particulate includes macrolide in crystalline form, the method comprising steps (a) and (b). In step (a) a composition is prepared that includes a macrolide, a first solvent, and a second solvent selected from the group consisting of an alcohol, acetone, and acetonitrile. The composition is characterized as providing a maximum solubility for the macrolide that is greater than a maximum solubility of the macrolide dissolved in either the first or second solvent individually. In step (b) the first and second solvents are evaporated from the composition to provide the macrolide particulates.

A third embodiment of the disclosure is also directed to a method (e.g., method III) for preparing macrolide particulates having a mean size of 20 μm or less, wherein the particulate includes macrolide in crystalline form, where in step (a) a composition is prepared that includes a macrolide, a first solvent that is aromatic, and a second solvent selected from the group consisting of an alcohol, acetone, and acetonitrile. In step (b) the first and second solvents are evaporated from the composition to provide the macrolide particulates.

In step (a) the composition can be formed using sub-steps (a1) and (a2). In step (a1) a pre-composition is formed wherein the macrolide is mixed with the first solvent and is present in an amount greater than its maximum solubility, such as where the pre-composition is in the form of a slurry. In step (a2), the second solvent is added to the pre-composition to completely dissolve the macrolide.

In embodiments, the first solvent can be an aromatic solvent selected from the group consisting of xylene, benzene, and toluene. In embodiments, the second solvent can be selected from the group consisting of methanol, ethanol, and isopropanol, particularly ethanol.

In embodiments, the majority of macrolide particulates have size (mean size) in the range of 0.4 μm to 4 μm.

In some cases the macrolide is a "non-antibiotic" macrolide such as rapamycin (sirolimus), fujimycin (tacrolimus), pimecrolimus, zotarolimus, everolimus, temsirolimus, or ridaforolimus/deforolimus. In some embodiments the macrolide is rapamycin.

Other embodiment of the disclosure are directed to macrolide particulates per se, the macrolide particulates having a mean size of 20 μm or less, or 10 μm or less, wherein the particulates include macrolide in crystalline form. Methods of the disclosure can be used to prepare a plurality of macrolide particulates having a mean size of 20 μm or less, or 10 μm or less, wherein there is a low degree of size dispersity (i.e., a low polydispersity) among the plurality of particulates. Macrolide particulates with a low polydispersity tend to have fewer particulates among the plurality of particulates of a size that considerably deviates from the mean particulate size of the set.

A set of macrolide particulates with low polydispersity can be particularly desirable for drug delivery applications including injectable compositions and implantable medical devices. Composition or device preparation can be improved, and more desirable release profiles can be achieved. For example, a macrolide particulate set with a low degree of polydispersity can be used to prepare a macrolide particulate-containing coating, which has uniform coating properties, and which can release the macrolide therapeutic in a more predictable manner in the body. Therefore, low polydispersity of the particulates and the macrolide in crystalline solid state can facilitate the preparation of compositions and devices with well-controlled and prolonged release profiles.

Other embodiments of the disclosure are directed to therapeutic compositions and medical devices comprising the macrolide particulates. For example, the macrolide particulates can be introduced into a subject by injection, or can be used in a delivery system that modulates release of the macrolide. In some aspects, the macrolide particulates are used to deliver macrolide therapeutic at an intravascular location. In some embodiments, the macrolide particulates are used in association with an implantable or insertable medical device. The macrolide particulates can be associated with the device, in a manner that they are releasable from, immobilized on, or immobilized within the device, or combinations thereof.

The macrolide particulates can also be used in conjunction with a polymer system that modulates release of the macrolide therapeutic. The polymer system can be biostable or biodegradable. In some cases the macrolide particulates are associated with a polymeric matrix, and the matrix can be associated with an implantable medical device, such as in a coating on a surface of the device. The macrolide particulates can also be immobilized in an in-situ formed body of polymeric material (such as a crosslinked hydrogel).

DETAILED DESCRIPTION

Figure 1A:
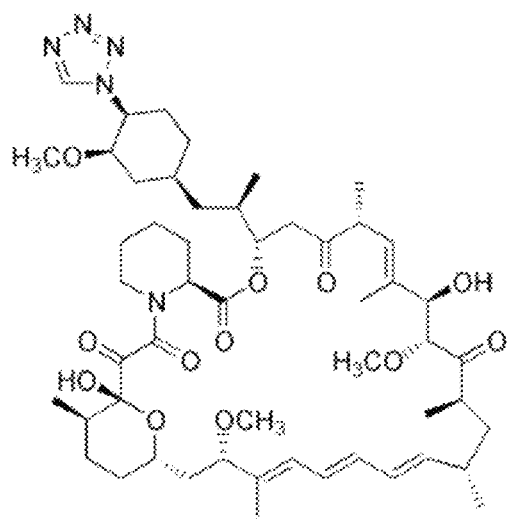
FIGS. 1A-G illustrate chemical structures of various non-antibiotic macrolides.
Figure 1B:
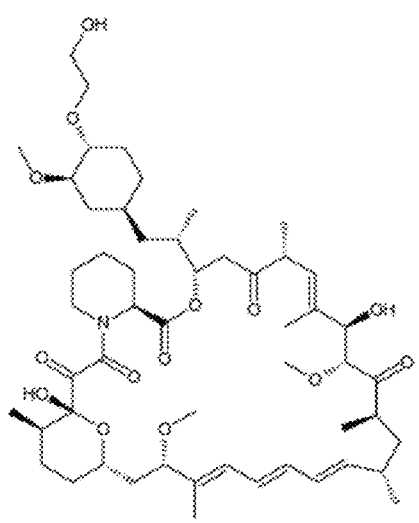
Figure 1C:
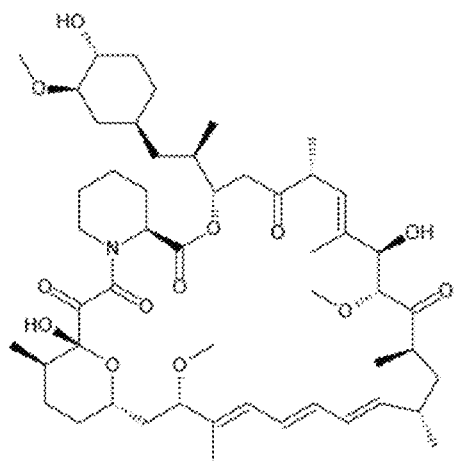
Figure 1D:
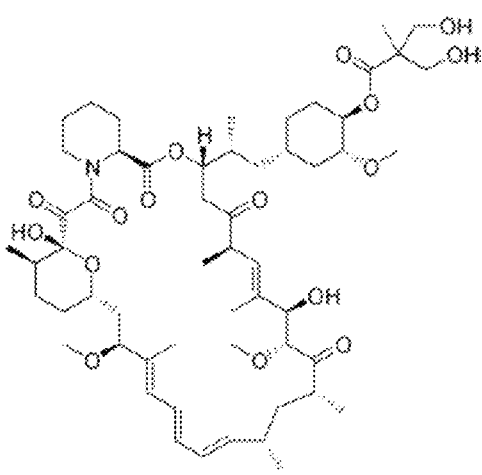
Figure 1E:
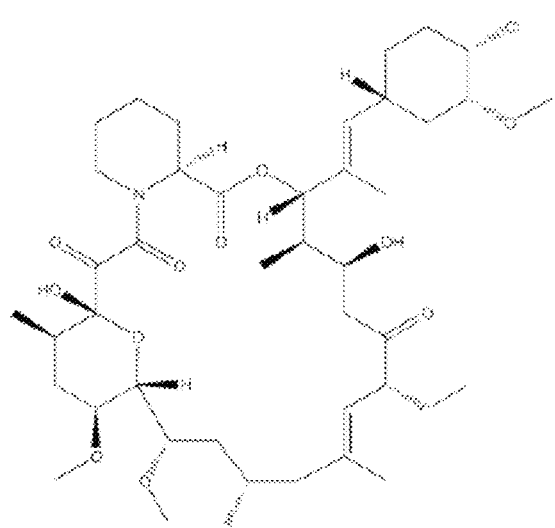
Figure 1F:
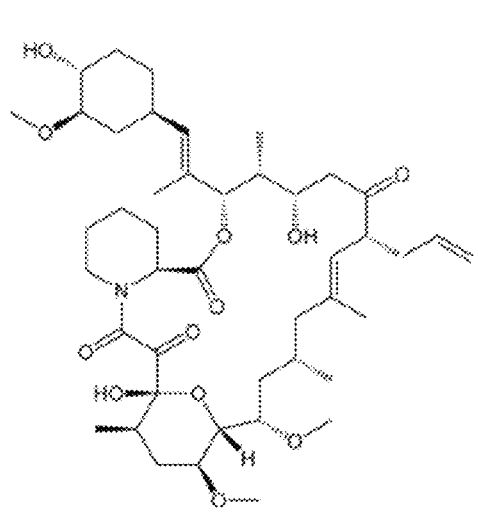
Figure 1G:
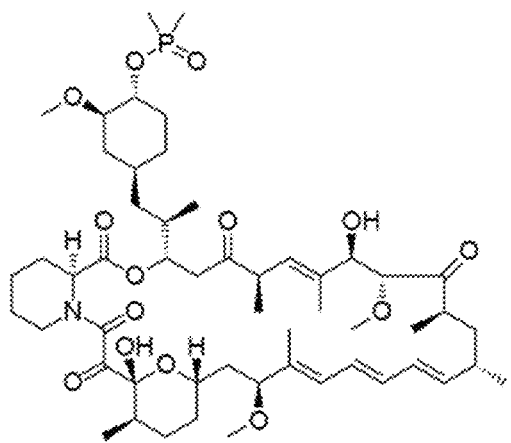

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present disclosure provides macrolide particulates that include macrolide in crystalline form in the particulate, methods for forming these particulates, and composition and medical devices associated with the macrolide particulates. The macrolide particulates have desirable properties including smaller sizes of 20 μm or less, or 10 μm or less, wherein the particulates include macrolide in crystalline solid state form. Methods of the disclosure can also provide a plurality of macrolide particulates including macrolide in crystalline form where, in the plurality of particulates, there is a low degree of size dispersity (i.e., low polydispersity).

In a treatment method, the macrolide particulates can be placed in a subject, alone or in association with a delivery article or composition, in a manner so the macrolide becomes therapeutically available to the subject. In some more specific delivery approaches, the macrolide particulates are associated with an implantable delivery article for the site-specific release of macrolide therapeutic.

Macrolides are characterized by a large macrocyclic lactone ring, which can be optionally defined by the number of atoms in the ring. The macrocyclic ring includes at least 7 ring atoms selected from carbon, nitrogen, oxygen, sulfur, silicon, phosphorous. Ring atom(s) can optionally be substituted with oxygen, and contain one or more degrees of unsaturation (double or triple bonds). Macrolide compounds of the present disclosure can include those that are multicyclic, such as bi- or tricyclic. Some macrolides include sugar molecules (e.g., two or more) bonded to the macrocyclic ring. Many macrolides are found as natural products and belong to the polyketide class of secondary metabolites from various prokaryotic and eukaryotic organisms. Many macrolide therapeutics are chemically synthesized derivatives of naturally-occurring macrolides. Use of non-antibiotic macrolides can be desirable for various indications, such as to prevent or minimize tissue response associated with inflammation, fibrosis, and thrombosis.

Non-antibiotic macrolides include rapamycin (e.g., sirolimus, RAPAMUNE™), everolimus (e.g., ZORTRESST™), pimecrolimus, temsirolimus, fujimycin/tacrolimus, deforolimus, zotarolimus, and biolimus. Chemical structures of some non-antibiotic macrolides are shown in FIG. 1.

Many of the non-antibiotic macrolides, such as rapamycin, have desirable immunosuppressive and antiproliferative properties. Rapamycin can inhibit growth factor- and mitogen-induced proliferation of T lymphocytes when the rapamycin-FKBP12 complex binds to an effector, and arrests the G1 to S transition of the cell cycle.

Rapamycin has a molecular weight of 914.17 g/mol and molecular formula: $C_{51}H_{79}NO_{13}$ (see also FIG. 1). It is insoluble in water, but soluble in ethanol (2 mM), methanol (25 mg/mL), DMSO (25 mg/mL), chloroform, (5 mg/mL), ether, acetone and N,N-dimethylformamide. As commercially supplied, rapamycin exists as one isomer (structurally homogeneous) in the solid form as indicated by X-rays whereas in solution there are two conformational isomers (approx. 4:1) which exist in equilibrium.

Figure 2:
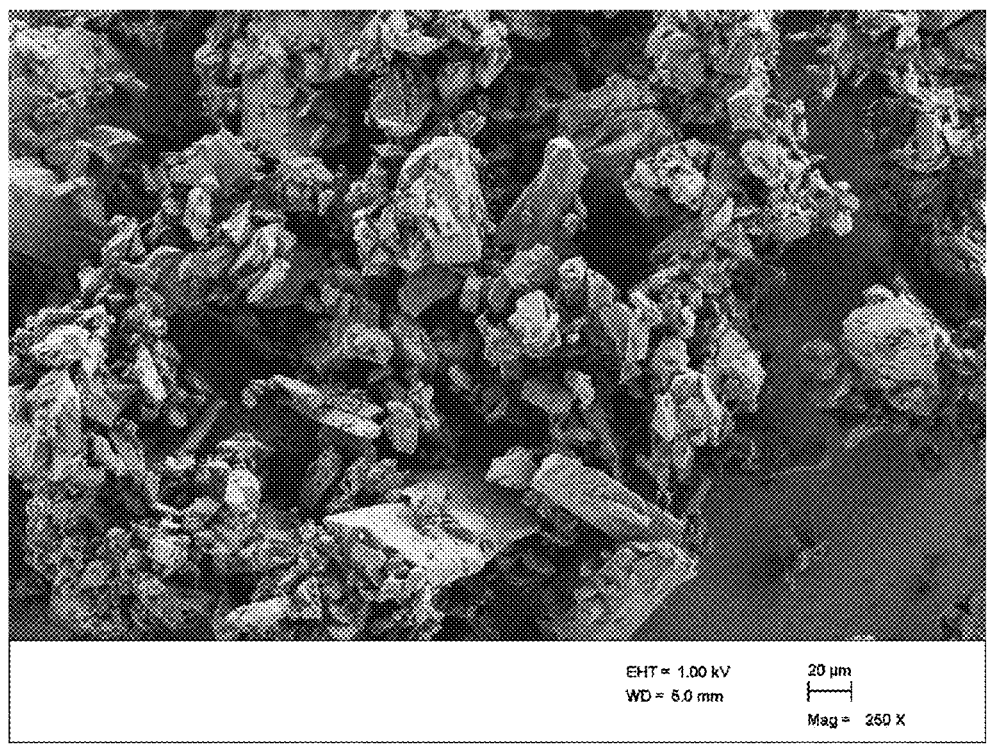
FIG. 2 is an electron micrograph of rapamycin powder obtained by making a slurry in o-xylene and subsequent evaporation of the solvent without stirring.

Rapamycin is commercially available as a manufacturer's preparation in powdered form (e.g., a "stock composition"). Observed using magnification, the powder can be in the form of flakes having irregular shapes (e.g., jagged outer surfaces) and of various sizes. The sizes of the flakes is rather large, having minimal dimensions of generally greater than about 25 μM, and more typically greater than about 100 μM (see FIG. 2). Stock compositions of rapamycin in powdered form are commercially available from various sources, such as LC Laboratories (Woburn, Mass.) and Sigma Aldrich. Other non-antibiotic macrolides, antibiotic macrolides, and ketolides, are commercially available, or can be prepared using techniques known in the art.

In embodiments, manufacturer's preparations can be subjected to method steps of the present disclosure to transform undesirable irregular-shaped and diverse-sized macrolide material (e.g., irregularly sized particles of larger than 20 μm) to desirably sized particulates where the particulates include macrolide in crystalline solid state form. In some embodiments, a manufacturer's preparation of macrolide in the form of irregularly sized particles of larger than 20 μm is subjected to a method of the disclosure to provide macrolide particulates having a mean size of 20 μm or less, wherein the particulates includes macrolide in crystalline form. The method can also provide a macrolide particulate preparation with low polydispersity. The method can avoid steps of crushing or grinding, which can be detrimental to activity, as well as crystalline morphology.

The macrolide compound, such as rapamycin, can optionally be subjected to any purification or enrichment process prior to being used to form the macrolide particulates. Exemplary optional purification or enrichment techniques include one or more affinity, hydrophobic, size exclusion, centrifugal, and liquid chromatographies (such as HPLC).

In some modes of practice, macrolide provided from a manufacturer's preparation can be added to a liquid to form a composition in an initial step in the process of preparing the particulates. The liquid can be a solvent for the macrolide. Exemplary liquids (e.g., macrolide solvents) in which the macrolide therapeutic can be dispersed and/or dissolved include aromatic hydrocarbons, such as benzene, xylene (e.g., ortho-xylene, para-xylene, or meta-xylene) and toluene; C1-C4 alcohols such as methanol, ethanol (EtOH), isopropanol (IPA), n-butanol, isobutyl alcohol and t-butyl alcohol; halogenated organic solvents such as dicholoroethane (DCE), dichloromethane (DCM), chloroform, and ethyl trifluoroacetate (ETFA); ketones such as methyl isobutyl ketone (MIBK), 3-pentanone (diethyl ketone) acetone, 2-butanone (MEK); acetonitrile (ACN); ethers such as isopropyl ether (IPE) and tetrahydrofuran (THF); aliphatic hydrocarbons such as hexane, heptane, or the like; esters such as ethyl acetate. Combinations or mixtures of solvents including two or more solvents can be used. In one mode of practice, the macrolide solvent comprises xylene, such as ortho-xylene.

Compositions prepared by method steps may optionally be referred to as a "first composition," "second composition," "third composition," etc. For example, in the first step, the composition may optionally be referred to as a "first composition" that includes the macrolide dissolved in the solvent or solvent mixture. In a subsequent step(s), if the composition is altered or changed, such as by the addition or removal of a material to or from the composition, the change may result in the formation of a "second composition."

As a general matter, the macrolide therapeutic can be dissolved and/or dispersed in a desired amount in a solvent, or mixture of solvents, for forming the macrolide particulates. As a general matter, dependent on the solvent or solvent combination, as well as the macrolide being dissolved, it is understood in the composition that the macrolide can display a maximum solubility at a predetermined temperature, such as about 20° C. At the maximum solubility a solution can be referred to as "saturated." The amount of macrolide dissolved can be described in conventional terms such as mg/mL, % (wt/vol), or molar. For example, the saturation point of rapamycin in many solvents is in the range of 15 mg/mL to 150 mg/mL. The addition of more macrolide to a saturated solution will cause formation of a supersaturated solution, or slurry, where a percentage of the macrolide in the composition is not dissolved but, for example, dispersed. Supersaturated solutions may be described in terms of the percentage of macrolide that is not dissolved, relative to the total amount (dissolved and undissolved) of macrolide in the composition.

A macrolide composition where the macrolide concentration is below the saturation level or "unsaturated" can also be described in conventional terms such as mg/mL, % (wt/vol), or molar. The concentration of macrolide in an unsaturated solution can also be described relative to its saturation level in the same solvent, such as a percentage of the saturation level. For example, rapamycin forms a saturated solution at about 75 mg/mL in xylene at 20° C.; which therefore is a 7.5% saturated solution.

In a step in the method of forming particulates according to method I, macrolide can be added to the solvent in an amount above the saturation point. Following addition, the composition can include macrolide in dissolved and non-dissolved states (e.g., as a dispersion). In some modes of practice, the macrolide can be added to the solvent in an amount of up to about 10% more than the saturation amount, up to about 15% more than the saturation amount, up to about 20% more than the saturation amount, or up to about 25% more than the saturation amount The vessel that the macrolide composition can be formed in, or eventually is placed in to, can be chosen based on one or more factors, such as a desired amount of macrolide particulates desired to be produced, or the subsequent steps performed in the method. The receptacle can be formed of plastic, glass, or metal, the inner surfaces of which can optionally be treated to minimize or eliminate any non-specific adsorption of the macrolide therapeutic to the surfaces. Exemplary thermoplastics receptacles are fabricated from polypropylene, polystyrene, poly(tetrafluoroethylene) (PTFE), and perfluoroalkoxy (PFA) polymers, such as Teflon™ and Neoflon™.

In method I, after the macrolide is dissolved and/or dispersed in a solvent or solvent mixture it can be subjected to a step of providing sonication in the dissolved macrolide composition. "Sonication" refers to the application of sound or ultrasound wave energy to agitate a composition. In the step of providing sonication, a device with a sonicating feature can be used, such as a sonicating tip or sonicating horn, etc. An ultrasonic processor can convert conventional alternating current to high frequency, high voltage electrical energy which is fed to a converter and transformed into mechanical vibration. Energy for the sound wave can be produced electronically and transported through a metallic tip of the sonicating device which is placed in the macrolide composition. The vibrating tip can cause compression and rarefaction waves from it surface. Sonication can provide cavitation in the sample, which is a rapid and repeated formation of microbubbles in the liquid composition that propagate microscopic shock waves to affect the macrolide composition in this method step.

Exemplary sonicating equipment that can be used in methods of the disclosure are commercially available, for example from Virtis (e.g., VIRSONIC™; Gardiner, N.Y.). Other sonicating devices include sonicating baths.

Sonication can be carried out at a desired temperature, such as in the range of about 5° C. to about 50° C. Sonication can also be carried out for a desired length of time, depending on the composition, composition size, and amount of energy to be delivered. For example, sonication can be carried out for a time period in the range of about 1 second to about 60 seconds, or about 5 seconds to about 30 seconds. Longer or shorter periods may be used depending on the composition size and sonication conditions. The step of sonication can be performed intermittently, with two or more periods of sonication performed interrupted with periods of no sonication. The sonication time may vary depending on the amount of macrolide present in the composition.

The sonication step can optionally be described with reference to one or more sonication parameters. For example, sonication step can optionally be described by the amount of power (e.g., measured in watts) over time (e.g., measured in joules) provided to the composition, such as the amount of power provided per unit volume of the composition, such as J/mL, or the amount of power provided per unit amount of macrolide present in the composition, such as J/mg. Power can be described as the energy required to drive the radiating surface of a sonicating tip or horn, at a specified amplitude of vibration, against a specified load, at the resonant frequency of the device.

The ultrasonicator can include a timer to set a desired sonication time. Based on the known volume of the test liquid, the specific sonication energy per minute can be described in terms of $kJ/m^3$. Hence, the sonication energy can be obtained as the specific sonication energy per minute multiplied by the sonication time. For the pulse mode, the sonication energy can be calculated as the energy at the continuous mode multiplied by the percentage of the 'on' time (e.g., 20% for the pulse 20 mode). Intensity is a measure of energy available per unit volume of sample and directly related to amplitude.

In method I, following sonication, a step of mechanically stirring and evaporating the composition can be performed. In this step the sonicated macrolide composition is stirred and the solvent or solvent mixture is allowed to evaporate over a period of time. A supersaturated composition can become more supersaturated during the step of stirring and evaporating, or in some embodiments a supersaturated composition is formed during the step. Evaporation can take place at normal or ambient pressure conditions, or the composition can be placed in a reduced pressure conditions to promote more rapid evaporation of the solvent from the composition. As the solvent evaporates the concentration of the macrolide can increase in the composition. In some modes of practice, if the composition is below the saturation point during the evaporation, the saturation point can be crossed and a supersaturated composition can be formed.

Stirring can be performed manually or using stirring equipment. Exemplary stirring equipment includes magnetic stir bars and magnetic beads. In an exemplary mode of practice, the sonicated macrolide composition is placed in a vessel such as a glass beaker with a magnetic stir bar and then stirred in a slow to medium setting over a period of time. The vessel can be of suitable size and configuration to promote evaporation of the solvent from the composition during the stirring step. For example, cylindrically shaped beakers can be used. Optionally, the stirring step may be described in terms of the liquid area exposed to air over the total volume of the composition (e.g., as measured when the composition is at rest). For example, in a cylindrical glass beaker having a predetermined diameter, a desired volume of composition can be added to the beaker at the onset of stirring (prior to solvent evaporation) to provide a desired surface area/volume ratio ($cm^2$/mL).

Stirring/evaporation can be carried out at a desired temperature, such as in the range of about 5° C. to about 50° C. Stirring/evaporation can be carried out normal atmospheric pressures (e.g., about 95 kPa to about 105 kPa) but may optionally be carried out under reduced pressure. Stirring and evaporation can also optionally be carried out in an area that can provide increased airflow across the solvent-exposed surface, such as in a laminar flow hood.

Evaporation of the solvent from the composition can be performed at a desired rate. The evaporation rate can be described in any one of a number of ways, such as the loss of volume per amount of time, or the percentage (volume) of loss of the composition per time, or the percentage (volume) of loss of the composition during the period of stirring and evaporation. During the period of stirring and evaporation, evaporation may initially proceed at a first rate, and then this rate may decrease over the period as the composition becomes more concentrated. In some modes of practice, during the step of stirring and evaporating, an amount of solvent in a desired range is evaporated from the composition. Stirring and evaporation parameters, as well as composition size, can be chosen so the solvent evaporates in a desired time period, such as in the range of hours or days.

Macrolide particulates can form in the composition during steps of the method I. Macrolide particulates can be present in the composition in the form a slurry, and the slurry can be stirred and thicken as solvent evaporates. Continued evaporation of solvent from the supersaturated solution can increase the amount of formed macrolide particulates. Evaporation of solvent can be carried out to a point where there is still solvent remaining in the vessel, but the stirring action does not cause substantial undesirable grinding of the macrolide particulates (e.g., substantial dry grinding).

The point at which stirring and evaporation is stopped can be described in one more ways. For example, it can be described in terms of the amount of solvent evaporated from the composition from the start to the end of the stirring and evaporation step, such as a desired percentage range of solvent being evaporated from the composition. It may also be described in terms of the percentage (wt.) of macrolide that is in the particulate (non-dissolved) state compared to the amount remaining dissolved in solvent.

After the stirring and evaporation step is completed, in method I a step of removing the remaining solvent from the composition can be performed. In some modes of practice the solvent is simply left to evaporate from the composition, forming a dry cake of material including the macrolide particulates. Other conventional solvent removal methods, such as filtration separation, can be used. If such an approach is taken, the filters desirably have pore sizes that prevent most or all formed macrolide particulates from moving through the filter. The solvent removed may include dissolved macrolide not formed into macrolide particulates, and this optionally can be reused to make another batch of macrolide particulates.

In the second and third method embodiments of the disclosure (method II and III), as a step in particle preparation, macrolide provided from a manufacturer's preparation can also be added to a solvent (e.g., a "first solvent"). Exemplary macrolide solvents in which the macrolide therapeutic may be subjected to include aromatic hydrocarbons, such as benzene, xylene (e.g., ortho-xylene, para-xylene, or meta-xylene) and toluene. In one mode of practice, the macrolide solvent of method II or III comprises xylene, such as ortho-xylene.

As a general matter, depending on the solvent as well as the macrolide being dissolved, it is understood in the composition of method II or III the macrolide can display a maximum solubility at a predetermined temperature, such as about 20° C. "Unsaturated" and "saturated" macrolide-containing compositions are described herein.

In an initial step of the method II or III, the macrolide therapeutic can be mixed with a solvent. Macrolide is added to the solvent in an amount above the saturation point. Following addition, the composition can include macrolide in dissolved and non-dissolved states (e.g., as a dispersion). In some modes of practice, the macrolide can be added to the solvent in method II or III in an amount of up to about 10% more than the saturation amount, up to about 15% more than the saturation amount, up to about 20% more than the saturation amount, or up to about 25% more than the saturation amount.

The vessel that the macrolide composition can be formed in, or eventually is placed in to, according to method II or III can be any one known in the art, including those described with reference to method I.

In method II or III, after preparing the slurry of the macrolide and the first solvent, a second solvent is added to the slurry. The second solvent can be selected from the group consisting of an alcohol, acetone, and acetonitrile. For example, the second solvent is selected from the group consisting of methanol, ethanol, and isopropanol, and in particular, the second solvent is ethanol.

During the addition of the second solvent, the undissolved macrolide in the slurry becomes dissolved. In modes of practice, the second solvent is added to the slurry in an amount wherein the macrolide becomes fully dissolved in the mixture of the first and second solvents. In some cases, the first solvent and second solvent are present in a volume ratio in the range of 50:50 to 90:10, respectively, or more specifically in a volume ratio in the range of 60:40 to 80:20, respectively.

In method II or III, the composition comprising the first and second solvents may, in some embodiments, be characterized as providing a maximum solubility for the macrolide that is greater than a maximum solubility of the macrolide dissolved in either the first or second solvent individually. For example, in the composition with the first and second solvent, the macrolide is present at a concentration of up to 200 mg/mL, or in some aspects, the macrolide is present in the composition at a concentration in the range of 75 mg/mL to 175 mg/mL. Stirring can be performed manually or using stirring equipment to aid in mixing of the first and second solvents and dissolution of the macrolide therapeutic.

The composition with the macrolide therapeutic, and first and second solvents can optionally include one or more excipient compound(s). One type of excipient compound that can be included in the composition is an antioxidant, which may in some cases be in mixture with the macrolide therapeutic as provided from a manufacturer's composition. The amount of 0.5% w/w. Pharmaceutically acceptable antioxidants are known in the art, for example, substituted phenols such as butylated hydroxytoluene (BHT), ascorbic acid (vitamin C), carotenes such as retinol (vitamin A), tocopherol (vitamin E), and glutathione.

In method II or III, after the composition including the first solvent, second solvent, and macrolide therapeutic is prepared, the solvent can be evaporated from the composition to provide the macrolide particulates. Evaporation can be carried out at a desired temperature, such as in the range of about 5° C. to about 50° C. Evaporation can be carried out normal atmospheric pressures (e.g., about 95 kPa to about 105 kPa) but may optionally be carried out under reduced pressure. Evaporation can also optionally be carried out in an area that can provide increased airflow across the solvent-exposed surface, such as in a laminar flow hood.

In one mode of practice, in method II or III the step of evaporating further comprises stirring the composition under the flow of an inert gas, such as nitrogen. To perform this, nitrogen gas can be passed into the evaporation vessel through a conduit, such as a glass pipette, placed at a desired distance above the surface of the solution. In another mode of practice, the top of the container from which the solvent is being evaporated can be sealed with a lid that has ports for the inflow and the exhaust of the inert gas. The inert gas such as nitrogen can be fed into the sealed container at a desired flow rate to promote evaporation of the solvent mixture from the composition.

In method II or III, evaporation of the solvent from the composition can be performed at a desired rate. The evaporation rate can be described in any one of a number of ways, such as the loss of volume per amount of time, or the percentage (volume) of loss of the composition per time, or the percentage (volume) of loss of the composition during the period of stirring and evaporation. During the period of stirring and evaporation, optionally, evaporation may initially proceed at a first rate, and then this rate may decrease over the period as the composition becomes more concentrated. In some modes of practice, during the step of stirring and evaporating, an amount of solvent in a desired range is evaporated from the composition. Evaporation parameters, as well as composition size, can be chosen so the solvent evaporates in a desired time period, such as in the range of hours or days.

Macrolide particulates having a size of 20 μm or less with desirable physical properties can form in the composition during the evaporation step in method II or III. As the first and second solvents evaporate, the composition can return to a slurry form, but now with the macrolide therapeutic in the form of the small particulates (≤20 μm) having low polydispersity. The slurry can thicken as solvent evaporates. Continued evaporation of solvent from the slurry can increase the amount of formed macrolide particulates. An amount of solvent can be evaporated so the composition is in the form of a slurry, a wet cake, or a dry cake.

In some modes of practicing method II or III, evaporation can be performed without any applied agitation (e.g., stirring) of the composition. The solvents can be evaporated from the composition to a desired form, such as a slurry, a wet cake, or a dry cake.

In some modes of practicing method II or III, evaporation can also be performed while the composition is being stirred. Stirring can be performed manually or using stirring equipment. Exemplary stirring equipment includes magnetic stir bars and magnetic beads. In an exemplary mode of practice, the macrolide composition is placed in a vessel such as a glass beaker with a magnetic stir bar and then stirred in a slow to medium setting over a period of time. The vessel can be of suitable size and configuration to promote evaporation of the solvent from the composition during the stirring step and can include a sealed with ports for the inflow and the exhaust of the inert gas. Evaporation of solvent can be carried out to a point where there is still solvent remaining in the vessel, but the stirring action does not cause substantial undesirable grinding of the macrolide particulates (e.g., substantial dry grinding).

Optionally, the stirring step may be described in terms of the liquid area exposed to air over the total volume of the composition (e.g., as measured when the composition is at rest). For example, in a cylindrical glass beaker having a predetermined diameter, a desired volume of composition can be added to the container at the onset of stirring (prior to solvent evaporation) to provide a desired surface area/volume ratio ($cm^2$/mL).

The point at which stirring and evaporation is stopped in method II or III can be described in one more ways. For example, it can be described in terms of the amount of solvent evaporated from the composition from the start to the end of the stirring and evaporation step, such as a desired percentage range of solvent being evaporated from the composition. It may also be described in terms of the percentage (wt.) of macrolide that is in the particulate (non-dissolved) state compared to the amount remaining dissolved in solvent.

If the solvents are not completely evaporated from the composition in method II or III, a step of removing the remaining solvent from the composition can be performed. In some modes of practice the solvent is simply left to evaporate from the composition, forming a dry cake of material including the macrolide particulates. Other conventional solvent removal methods, such as filtration separation, can be used. If such an approach is taken, the filters desirably have pore sizes that prevent most or all formed macrolide particulates from moving through the filter. The solvent removed may include dissolved macrolide not formed into macrolide particulates, and this optionally can be reused to make another batch of macrolide particulates.

In method II or III, after the macrolide particulates are formed, with all or a portion of the solvents are removed from the composition, a non-solvent can be added to the particulates. An exemplary non-solvent is water, but any liquid or liquid mixture that does not cause the macrolide particulates to dissolve can be used.

Optionally, after the non-solvent is added to the macrolide particulates, sonication can be performed in the macrolide therapeutic/non-solvent composition. "Sonication" refers to the application of sound or ultrasound wave energy to agitate a composition, and a device with a sonicating feature can be used, such as a sonicating tip or sonicating horn, etc. Exemplary sonicating equipment that can be used in methods of the disclosure are commercially available, for example from Virtis (e.g., VIRSONIC™; Gardiner, N.Y.). Other sonicating devices include sonicating baths. Sonication can aid in dispersing or separating the macrolide particulates.

The formed macrolide particulates made according to any one of method I, II, or III can optionally be subjected to one or more analysis techniques to assess physical properties, including size, shape, dispersity, and crystallinity of the particulates. For example, marcrolide particulate preparations can be analyzed by microscopy, such as by light microscopy, by scanning electron microscopy (SEM), by wide angle X-ray scattering (WAXS), and DSC. Microscopy can be used to understand the general characteristics of macrolide particulate preparation. The visible external shape of the macrolide particulate as observed by microscopy can be referred to as the particulate's crystal habit. For example, the crystal habit of the particulate can include a shape such as rhomboidal, dodecahedral, hexagonal, stellate, coxcomb, cubic, octahedral, tetragonal, orthorhombic, monoclinic, or triclinic.

The particulate can also optionally be described in terms of the macrolide being in a particular chemical state, such as where the solid form is present as a hydrate, dehydrate, salt, solvated, or desolvated, or combinations of these forms. Liquid molecules, such as a solvent or water, among the crystalline macrolide particulate can be referred to as adducts or co-adducts. If present, the adduct or co-adduct may be present in a stoichiometric amount relative to the amount of macrolide, or present in a non-stoichiometric amount relative to the amount of macrolide, such as where water or solvent molecules are arbitrarily positioned within the crystal lattice of the macrolide particulate. If present, water or solvent adduct or co-adducts may optionally be removed from the crystal lattice to provide macrolide particulates that may be referred to as dehydrates or desolvates. This process may leave voids and/or holes in the crystal lattice of the particulate.

The particulate may also have the macrolide in a particular crystalline polymorphic form in the crystalline lattice (e.g., a distinct crystalline species). A macrolide particulate wherein the macrolide is in a particular polymorphic form can provide the particulate with particular properties, such as solubility, melting point, hardness, crystal shape, and optical and electrical properties, and these may differ among different polymorphs.

Figure 6:
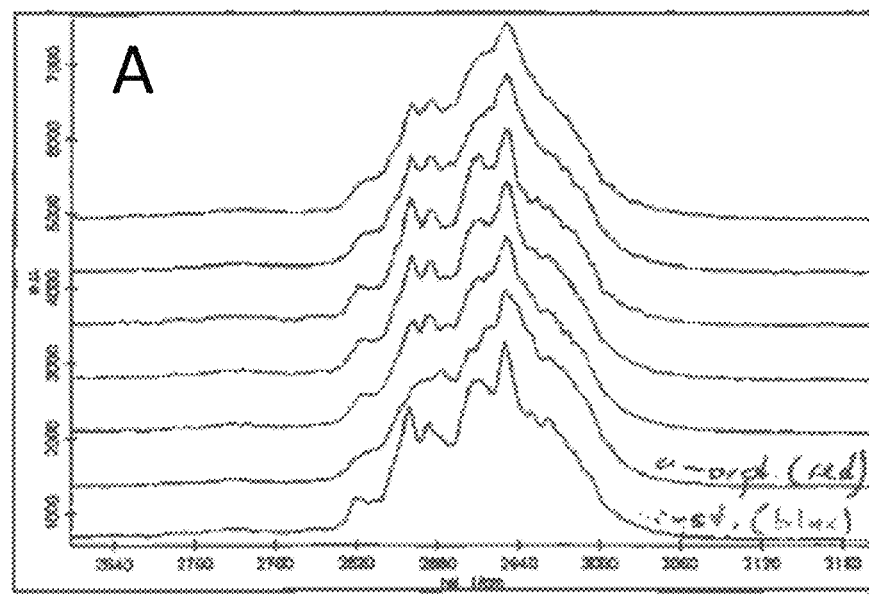
FIGS. 6a and 6b are RAMAN spectra of amorphous and crystalline forms of rapamycin.
Figure 6:
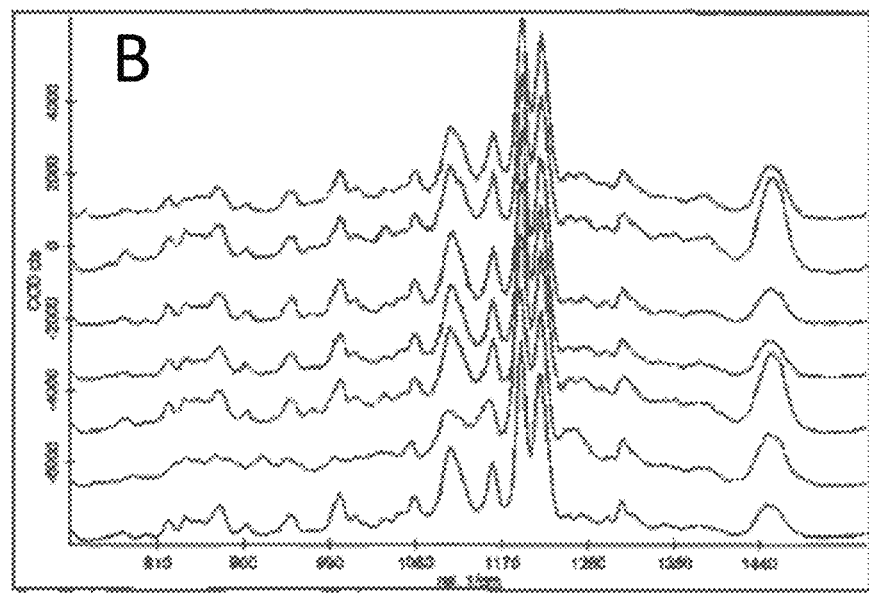
Figure 7:
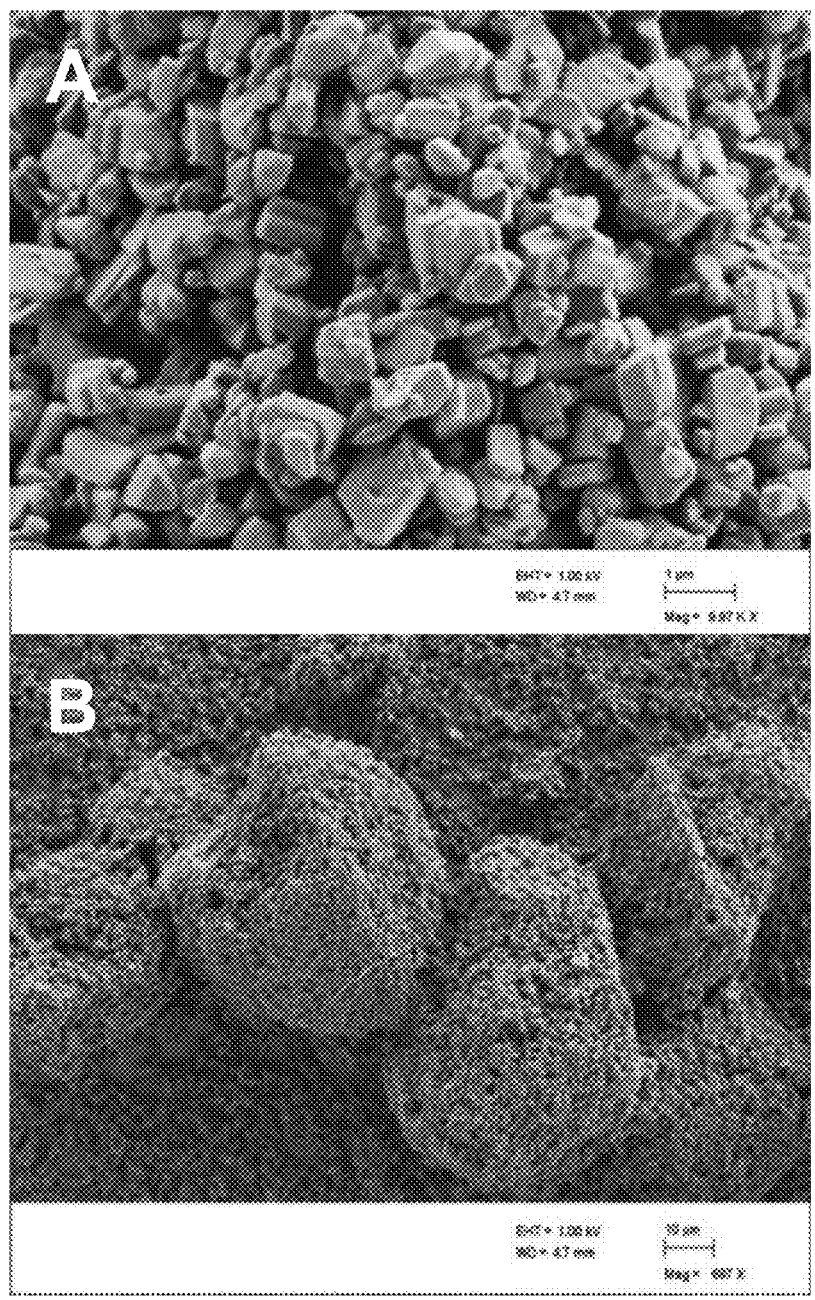
FIGS. 7A (9.97 K× magnification) and B (697× magnification) are electron micrographs, and FIG. 12 a size distribution histogram generated by laser light scattering analysis, of rapamycin crystalline particulates obtained using a mixture of o-xylene and methanol.
Figure 8:
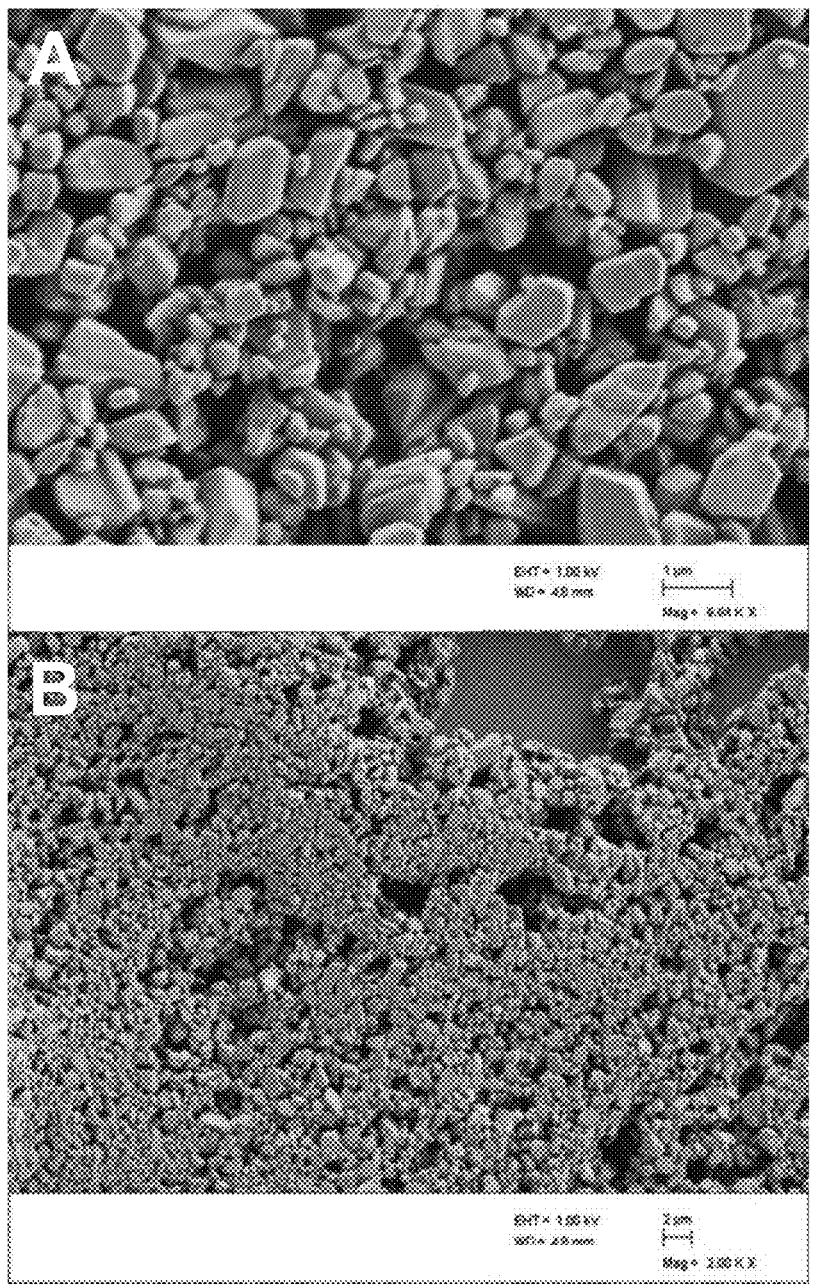
FIGS. 8A (9.94 K× magnification) and B (2.00 K× magnification) are electron micrographs, and FIG. 13 a size distribution histogram generated by laser light scattering analysis, of rapamycin crystalline particulates obtained using a mixture of o-xylene and ethanol.
Figure 9:
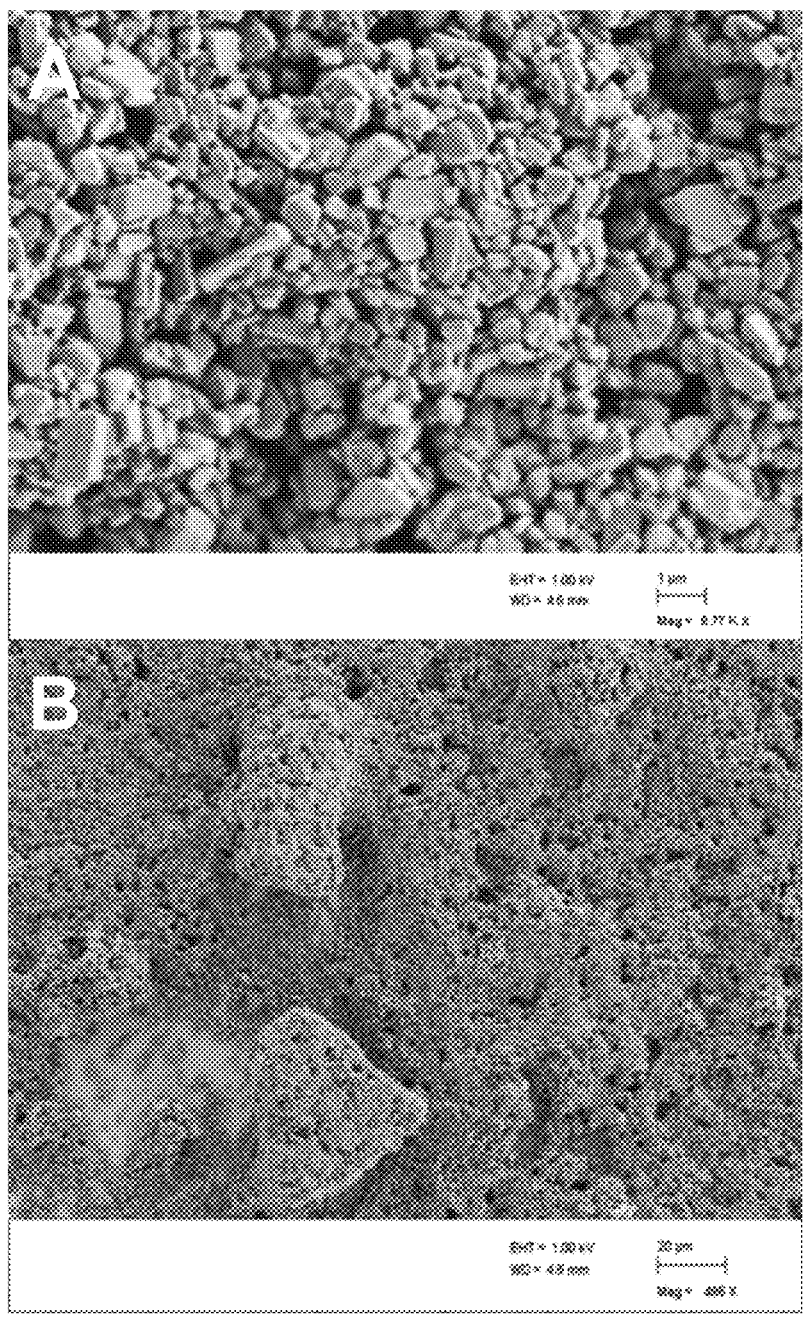
FIGS. 9A (6.77 K× magnification) and B (486× magnification) are electron micrographs, and FIG. 14 a size distribution histogram generated by laser light scattering analysis, of rapamycin crystalline particulates obtained using a mixture of o-xylene and isopropanol.
Figure 10:
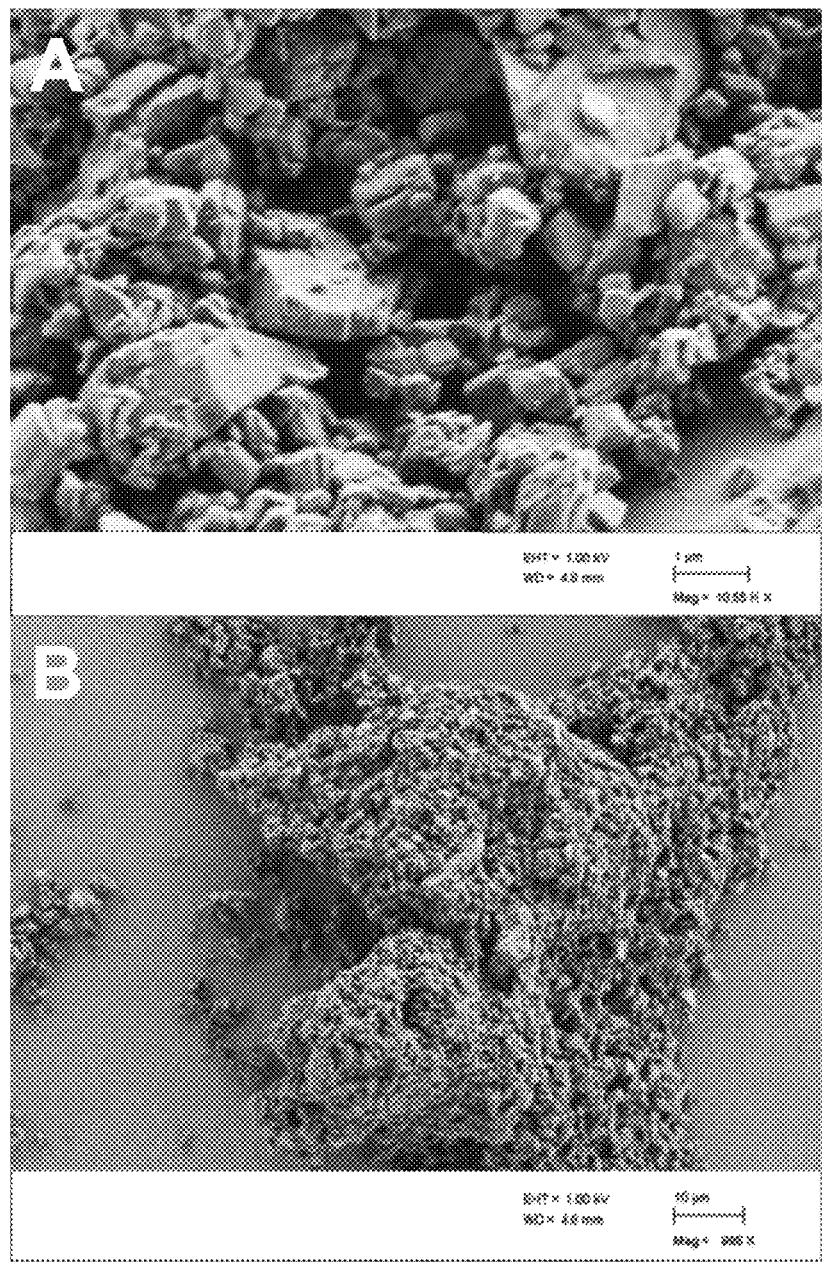
FIGS. 10A (10.55 K× magnification) and B (996× magnification) are electron micrographs, and FIG. 15 a size distribution histogram generated by laser light scattering analysis, of rapamycin crystalline particulates obtained using a mixture of o-xylene and acetone.
Figure 11:
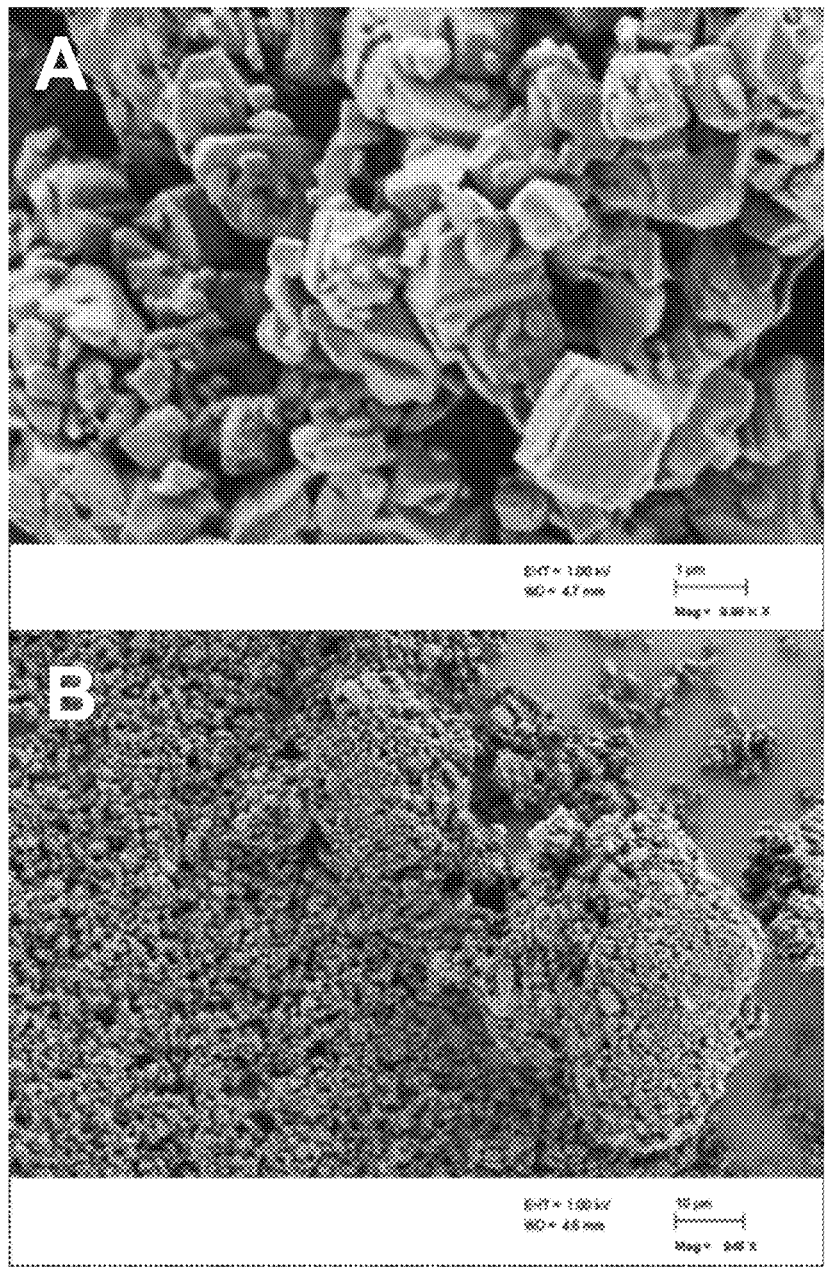
FIGS. 11A (9.99 K× magnification) and B (945× magnification) are electron micrographs, and FIG. 16 a size distribution histogram generated by laser light scattering analysis, of rapamycin crystalline particulates obtained using a mixture of o-xylene and acetonitrile.
Figure 12:
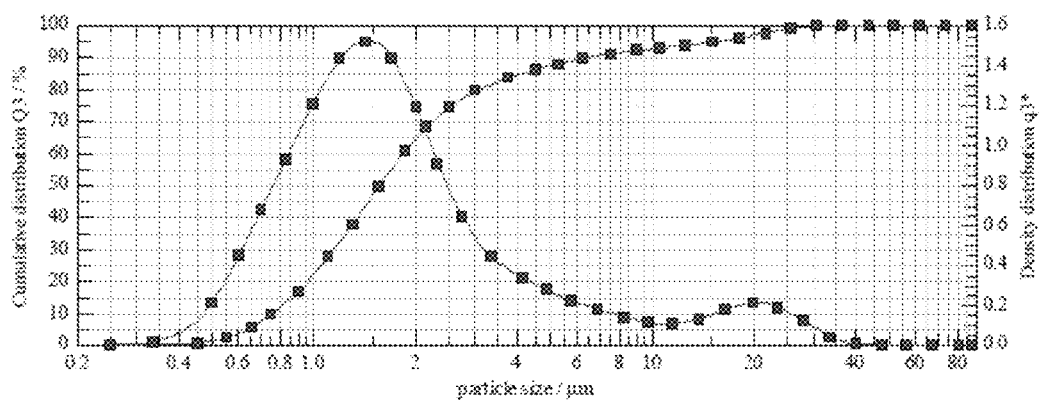
FIGS. 12-16 are particle size distribution histograms corresponding to the particles shown in FIGS. 7-11, respectively.
Figure 13:
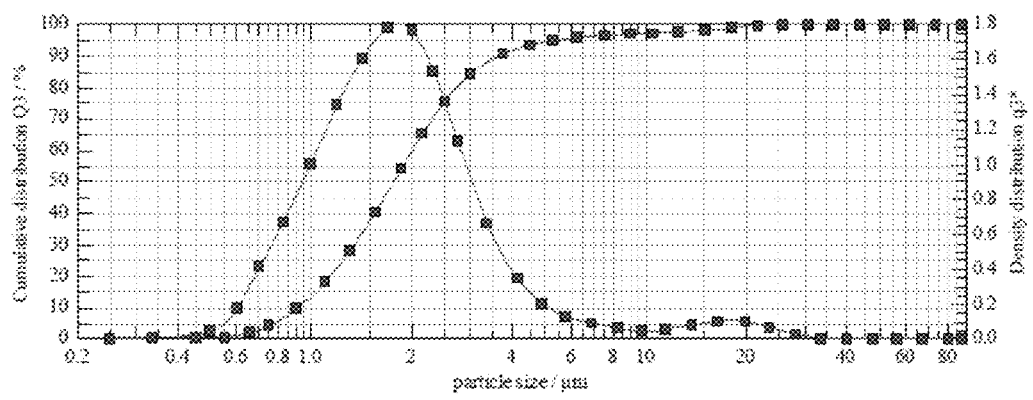
Figure 14:
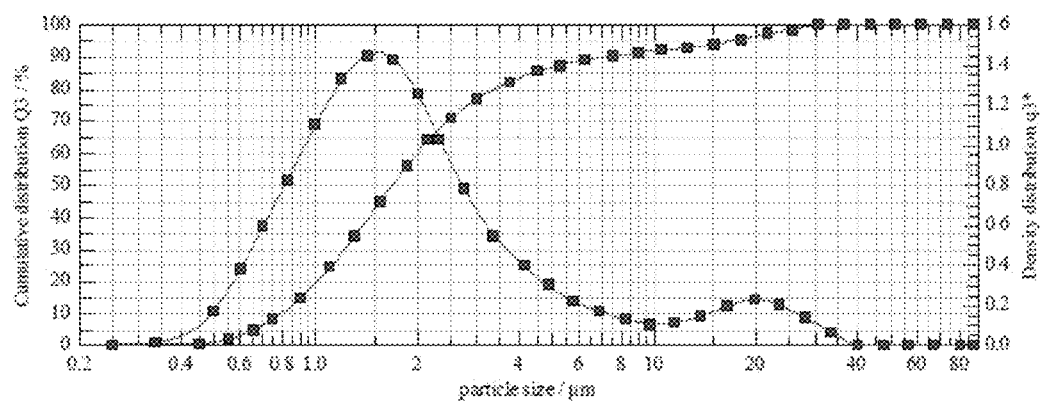
Figure 15:
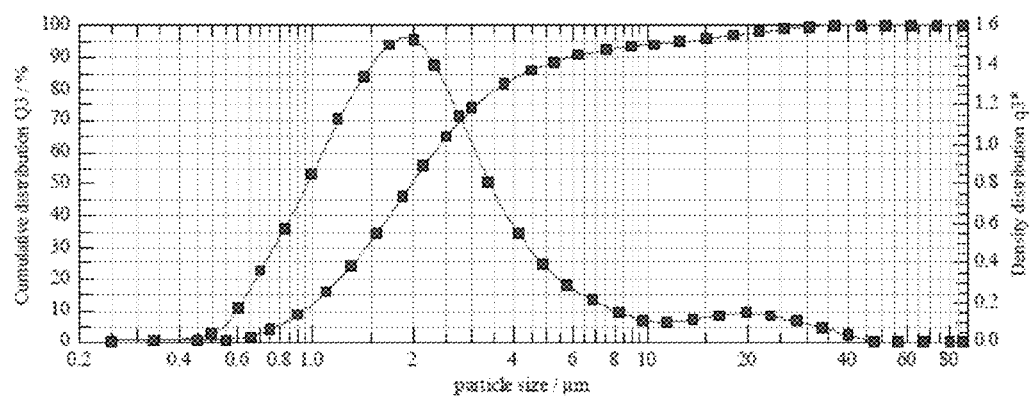
Figure 16:
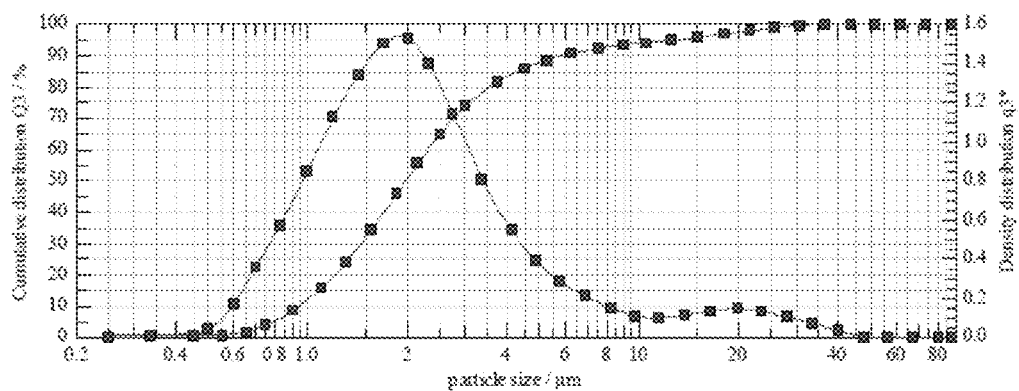
Figure 17:
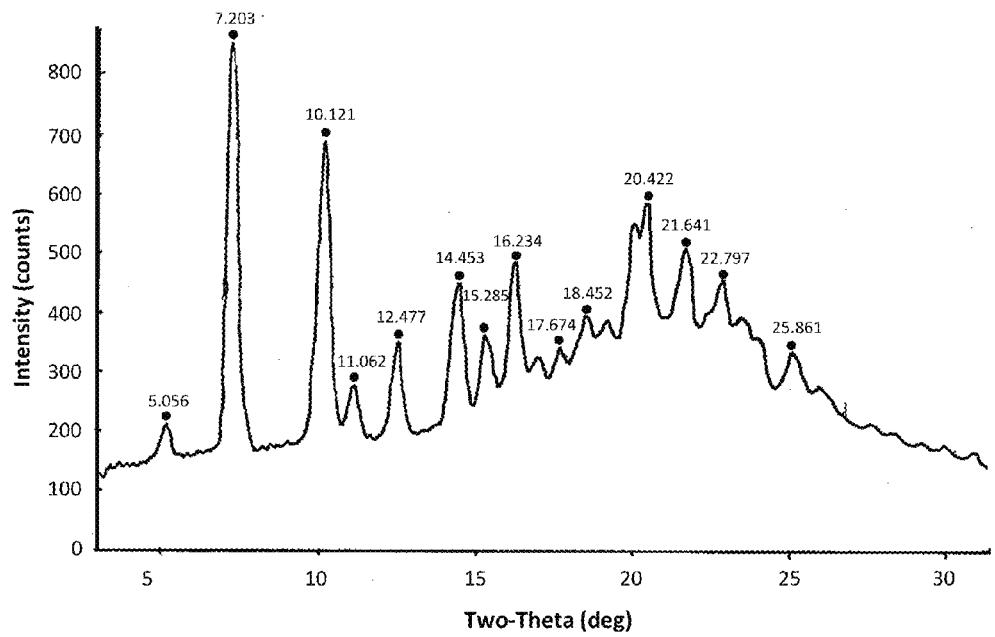
FIG. 17 is an XRD spectrum of particles of the present disclosure.

Raman spectroscopy can be used to analyze crystallinity in a sample, and can be used to distinguish over particulates where the macrolide is in amorphous form. Raman analysis of particulates where the macrolide is in crystalline solid will generally show spectrum peaks that are higher and sharper than when the macrolide is in amorphous solid form (see, for example, FIGS. 6a and 6b). Particulates with partially crystalline rapamycin will have Raman peak profiles that are between the fully crystalline and fully amorphous states. Computer software can be used to measure peak width and intensity to provide a quantitative measure of crystallinity.

The particulates can optionally be described in terms of the percent of the particulate that includes the macrolide in crystalline form. For example, the macrolide, such as rapamycin, can be in crystalline solid state form in an amount of about 50% (wt) or greater, about 60% (wt) or greater, about 70% (wt) or greater, about 80% (wt) or greater, about 90% (wt) or greater, about 95% (wt) or greater, about 98% (wt) or greater, about 99% (wt) or greater, about 99.5% (wt) or greater, or about 99.9% (wt) or greater, in the particulate.

Particle size and size distribution of a macrolide particulate preparation can be performed using any one of various techniques known in the art. In one mode of practice, laser diffraction can be used to measure particle size and distribution. In laser diffraction a laser beam passes through a dispersed particulate sample and angular variation in intensity of light scattered is measured. The angle of light scattering is greater for large particles and less for smaller particles, and the angular scattering intensity data can be collected and analyzed to generate a particle size profile.

Analysis of particulate size and distribution can be performed using laser light scattering equipment such as Malvern System 4700, (for particles from 1 nm to 3 μm) or Horiba LA-930 (e.g., for particles from 100 nm to 2 mm). The output from such analyzers can provide information on the sizes of individual macrolide particulates, and the overall amount of macrolide particulates of these sizes reflecting the distribution of macrolide particulates in terms of size. Analysis providing data on the size distribution can be provided in the form of a histogram, graphically representing the size and size distribution of all the macrolide particulates in a preparation.

The macrolide particulates produced according to the methods of the disclosure may have a particle size (mean; as measured through the particulate from one side to the other as in a diameter measurement) from about 100 nm to about 20 μm, more specifically from about 500 nm to about 10 μm, in the range of about 750 nm to about 7.5 μm, and even more specifically from about 1 μm to about 6 μm.

Shapes associated with particulates of this size include, but are not limited to rhomboidal, dodecahedral, hexagonal, stellate, coxcomb, cubic, octahedral, tetragonal, orthorhombic, monoclinic, or triclinic. The particulate may have a globular configuration but with an outer surface that includes jagged, flat surfaces, rather than a smooth spherical outer surface.

A preparation of the macrolide particulates may also be described in terms of size dispersity. Methods of the disclosure can be used to provide a preparation (e.g., a "batch" or "set") of a plurality of microparticles having desirable size characteristics, such as a low degree of size dispersity. A low size dispersity means there is less variation in the size of the particulates in the preparation (as compared to a high size dispersity, which means there is considerable variation in the size of the particulate). The degree of dispersity can be understood by histograms obtained by light scattering analysis.

In some embodiments, the method of the disclosure can provide a single mode macrolide particulate preparation. In a single mode macrolide particulate preparation, there will be a mean size of particulates determined by the particulate size for each particulate in the preparation, divided by the total number of the particulates in the preparation. The preparation can also have a size range, with the lower end of the range referring to the smallest particulates of the set, and the upper end of the range referring to the largest particulates of the set. The median size of the set (as compared to the mean, also referred to as the "mode" or "$x_{50}$") is the middle of the range.

Figure 5:
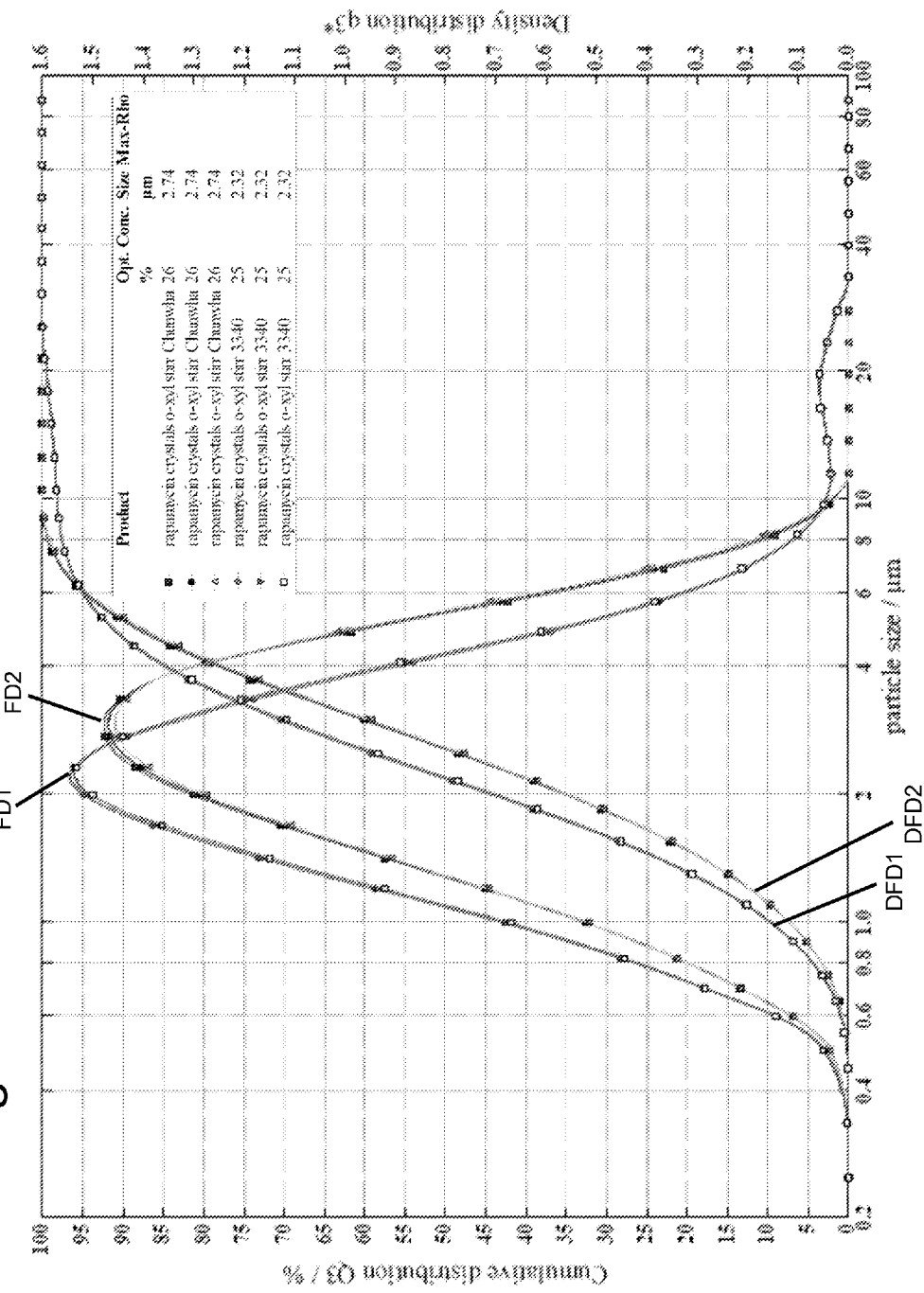
FIG. 5 is a size distribution histogram generated by laser light scattering analysis of rapamycin particulates having a mean particle size in the range of 2-4 microns.

In some cases, referring to FIG. 5, the size dispersity of particulate preparations is graphically represented in the form of frequency distribution curves (lines FD1 and FD2). From this curve, which is usually Gaussian shaped (e.g, "bell shaped"), one can correlate a specific particulate size (x axis) with the frequency (y axis on the left hand side of the graph) that particulates of this size are encountered in the set. The derivative of this curve (shown in FIG. 5 as line DFD1 and DFD2) represents the cumulative distribution of the particulates in the preparation. FIGS. 12-16 also show the size dispersity of particulate preparations graphically represented in the form of frequency distribution curves.

In some cases, the particle size distribution of the particulate preparation can be described by $x_{10}$, $x_{50}$ and $x_{90}$ values, which are defined as the particulate sizes calculated from the cumulative distribution curve at 10%, 50%, and 90% fractions of the total amount of particulates, respectively. For example, the particulate size where 10% of the total amount of particulates are smaller than or equal to that size is defined as the $x_{10}$. In some cases, the particulate preparation can be defined by the "degree of monodispersity" (DM) and determined by the following equation:

$$DM = (x_{90} - x_{10})/x_{50}$$

A particulate preparation is more homodisperse as the value of DM approaches 0.

The average size of particulates in the particulate preparation can be calculated knowing the mean size d of the particulates, which is calculated by summation of all products between number of particulates $n_1$ with size $d_1$ over all sizes i (area under the frequency distribution curve) and dividing that by the total number of particulates $\Sigma_i n_i$:

$$d = \frac{\sum_i n_i d_i}{\sum_i n_i}$$

The mode is defined as the particulate size at the maximum of the frequency distribution curve.

In one mode of preparation, method I produces for a particulate preparation that has a mean size of 2.3 µm (diameter), and (as derived from the frequency distribution curve of the set), a size at $x_{50}$ of 2.3 µm, a size at $x_{10}$ of 1.0 µm, and a size at $x_{90}$ of 4.4 µm, has a degree of monodispersity of 1.48. (the size difference within 80% of the particles ($x_{90} - x_{10}$) divided by the particle size at $x_{50}$, which is 1.48). In another mode of preparation, the method produces for a particulate preparation that has a mean size of 2.7 µm (diameter), and (as derived from the frequency distribution curve of the set), a size at $x_{50}$ of 2.5 µm, a size at $x_{10}$ of 1.1 µm, and a size at $x_{90}$ of 5.0 µm, has a degree of monodispersity of 1.56.

In one mode of preparation, method II or III produces for a particulate preparation that has a modal size of 2.7 µm (diameter), and (as derived from the frequency distribution curve of the set), a size at $x_{50}$ of 2.7 µm, a size at $x_{10}$ of 1.1 µm, and a size at $x_{90}$ of 6.2 µm, has a degree of monodispersity of 1.9. (the size difference within 80% of the particles ($x_{90} - x_{10}$) divided by the particle size at $x_{50}$). In another mode of preparation, the method produces for a particulate preparation that has a modal size of 3.4 µm (diameter), and (as derived from the frequency distribution curve of the set), a size at $x_{50}$ of 3.2 µm, a size at $x_{10}$ of 1.1 µm, and a size at $x_{90}$ of 11.7 µm, has a degree of monodispersity of 3.4.

To exemplify volume distribution of the microparticles, crystalline rapamycin microparticulates were prepared from evaporation of a o-xylene/ethanol solution in a stream of nitrogen gas was repeated five times at a 500 mg batch level. Particle size measurements using laser diffraction showed a normal Gaussian size distribution which was reasonably well controlled in the process. The average values and standard deviations are listed in Table 1. The values are calculated from volume-based size distributions, generally skewing data to give more weight to larger sizes.

TABLE 1

Average crystal size of rapamycin based on volume distribution by laser diffraction.

| Sample | X50 (µm) | X90 (µm) | X95 (µm) | X99 (µm) | mode |
|---|---|---|---|---|---|
| A | 270 | 621 | 7.81 | 15.9 | 2.74 |
| B | 3.06 | 7.25 | 8.94 | 15.66 | 4.11 |
| C | 3.00 | 7.86 | 11.39 | 27.14 | 3.35 |
| D | 2.73 | 6.82 | 11.17 | 28.40 | 3.35 |
| E | 3.15 | 11.70 | 20.10 | 36.49 | 3.35 |
| average | 2.99 | 8.41 | 12.90 | 26.92 | 3.54 |
| St dev | 0.18 | 2.24 | 4.93 | 8.58 | 0.38 |
| CV % | 6.1% | 26.6% | 38.2% | 31.9% | 10.7% |

According to the methods of the present disclosure, a particulate set with a low degree of monodispersity can be prepared.

In some aspects, the degree of monodispersity of the particulate set is about 5 or less, such as in the range of about 1 to about 5, about 4 or less, such as in the range of about 1 to about 4, about 3 or less, such as in the range of about 1 to about 3, about 2.5 or less, such as in the range of about 1 to about 2.5, or about 2 or less, such as in the range of about 1 to about 2, In some cases, the particulate set has a degree of monodispersity as described above, and particulate of the set have a modal size in the range of about 0.3 µm to about 10 µm (diameter), or a modal size in the range of about 0.5 µm to about 10 µm (diameter).

Size polydispersity can also be described in terms of a dispersity index, which is derived from an equation taking into account the size and distribution of particulates within the particulate preparation.

Size polydispersity "D" is defined by the weight average diameter (dw) of the set of particulates divided by the number average diameter (dn) of the set of particulates dw/dn)

The following definitions and equation is useful for determining size polydispersity.

$n_i$=the number of particle with diameter $d_i$
$d_i$=a particular diameter
$d_n$ (number average)=sum $n_i \times d_i$/sum $n_i$
$d_w$ (weight average)=sum $n_i \times d_i^2$/sum $n_i \times d_i$ The formed crystalline particulates may be optionally suspended in a non-solvent for preparation of a therapeutic composition, or for association with a medical device.

The macrolide particulates of the present disclosure can be delivered to a site within the body for the therapeutic treatment of a medical condition. In some modes of delivery, the macrolide particulates will slowly dissolve when placed in contact with a body fluid, and release the macrolide, such as rapamycin, which can provide a bioactive effect locally or systemically in the body.

In some preparations, the macrolide particulates are prepared to dissolve and release macrolide therapeutic in an aqueous environment, such as body fluid. Optionally, individual macrolide particulates can be provided with a very thin coating (e.g., "shell"), or can be encapsulated to further regulate release of the macrolide therapeutic, beyond the modulation provided by the crystalline form of the macrolide. In some cases, the coating or shell can be in contact with the outer surface of the particulate and have a thickness that is less than the diameter of the macrolide particulate per se. The coating or shell around the particulate may delay the release of the macrolide therapeutic from the particulates after placement within a patient. In some embodiments, the macrolide particulates can be included in a therapeutic liquid delivery composition. The liquid composition can be prepared for the delivery of the macrolide particulates via injection into a target location in the body. For example, the microparticle compositions can be formulated for subcutaneous, intramuscular, intravenous, intrathecal, intraperitoneal, or intraocular injections. The macrolide particulates in the liquid composition can optionally include a coating or can be encapsulated.

In some aspects, the macrolide particulates are associated with a system that controls the release of the macrolide therapeutic to the body. For example, the macrolide particulates can be included within an implantable medical device, such as in an internal reservoir of an implantable medical device. The body can include one or more apertures, or can have a membrane, and macrolide therapeutic can be released from the reservoir exiting the device through the apertures or membrane, upon which it can become available to tissue or fluid in a subject. Exemplary medical devices having apertures capable of releasing therapeutic are described in various references, such as described in commonly assigned U.S. Pub. No. 2008/0081064 (Anderson, et al.)

In some aspects, the macrolide particulates are associated with a polymeric matrix that can be placed or formed at a target location in the body. For example, the particulates can be entrained or entrapped within the polymeric matrix, associated with the surface of a polymeric matrix, or combinations thereof. The polymeric matrix may modulate release of the macrolide therapeutic by one or more modes of release modulation.

The polymeric matrix can be in the form of an in-situ formed polymeric matrix, or an implant. The polymeric matrix can also be associated with an implantable medical device, such as in the form of a coating on a surface of the device or a matrix within the device. The polymeric matrix can be biostable, biodegradable, or can have both biostable and biodegradable properties. The polymeric matrix can be formed from synthetic or natural polymers.

The macrolide particulates can be associated with a medical device, such as in a polymeric matrix associated with the medical device. In some cases, a particulate-containing coating can be formed on the surface of a medical article that can be introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, the macrolide particulates are associated with a balloon catheter, such as associated with a polymeric coating on a portion, or all of, the balloon surface. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion can be then fed over the guidewire until the balloon reaches the target location in the vessel. The balloon can be then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

The balloon can be formed from any material, or combination of materials, capable of expanding, and suitable for use within the body. The balloon can be made from an elastomer, which can be a thermoplastic polymer with elastic properties. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The balloon can be made of a single elastomeric material, or a combination of materials. The balloon can be manufactured by an extrusion process, so that the elastic portion can be a single layer of material, or co-extruded to form a multi-layered material.

The elastic portion can have a thickness suitable for the application and device described herein. For example, an exemplary thickness of an elastic portion can be in the range of about 0.005 mm to about 0.25 mm, or about 0.005 mm to about 0.1 mm, or about 0.005 mm to about 0.05 mm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon.

In some aspects, the balloon on which the macrolide particulates are associated with can be formed upon can be a macroscopically smooth, microporous, flexible, elastic tubular prosthetic device made from a substantially non-elastic woven fabric tube as described in U.S. Pat. No. 4,652,263. The exterior of the tube can be an easily deformed, macroscopically smooth surface having a multiplicity of interstices, or apertures, among the threads and among the fibers of the threads.

In some embodiments, apertures in the balloon can have openings of predetermined sizes suitable for a biocompatible liquid to be released and to affect release of transfer of the macrolide particulates from the balloon surface. In some aspects the apertures have a size in the range of about 0.0025 mm to about 2.5 mm, about 0.005 mm to about 1 mm, or about 0.01 mm to about 0.5 mm. The apertures in the balloon can be of any shape or combination of shapes, although a preferred shape of the apertures can be round. Other shapes such as oval and polygonal (triangular, square, rectangular, hexagonal) shapes are contemplated.

The balloon on which a coating with macrolide particulates can be formed can be commercially obtained, for example, from Atrium Medical (e.g., the ClearWay™ RX catheter having a 0.014" guidewire, 6 & 7 Fr guide catheter, 1-4 ATM Infusion Pressure, and 134 cm catheter working length).

The balloon can be inflated using a fluid, which can be injected through an inflation port. The mechanics of fluid transfer and introduction within balloons vary according to the specific design of the catheter, and are well known in the art.

A balloon catheter with the inventive microparticulate-associated surface of the disclosure can be used in a balloon angioplasty procedure. Balloon angioplasty can be carried out for the treatment of diseased arteries to reduce atherosclerotic stenosis or to recanalize occluded arteries. In such a procedure, obstructed intraluminal passages are reopened or dilated by inflation of the balloon at the occluded site. According to the disclosure, balloon catheter having a microparticulate associated balloon portion can be inserted percutaneously into a luminal passage of a patient, such as an artery, vein, or airway. Once inserted, the balloon can be advanced to the desired treatment site, where the balloon can be inflated to dilate the luminal passage.

In some modes of practice, upon inflation of the balloon, at least a portion of the microparticulates that are associated with the surface of the balloon are transferred to the tissue of lumenal arterial wall at the target site.

For example, in aspects wherein the microparticulates are included in an expandable coating on the surface of the balloon, the inflation of the balloon can stretch the coating. The coating on the surface of the balloon can undergo physical changes that promote the release of the macrolide particulates. Upon insertion in a subject, a coating that is in the form of a flexible hydrogel matrix can become more hydrated, resulting in a loosening of the matrix material around the macrolide particulates. Also, the stretching of the coating (upon balloon expansion) can cause it to effectively become thinner than the coating on the balloon in an unexpanded state. In addition, the stretching of the coating can create pores in the coating from which the macrolide particulates can escape. The hydration, thinning of the coating and/or the creation of the pores can effectively cause the macrolide particulates to "pop out" of the coating upon balloon expansion.

In yet other embodiments, macrolide particulates presently disclosed can be associated with various polymers (for example, but not limited to, poly(ethylenimine) and poly(vinyl amine)) for delivery to a mammal. Other applications and compositions are described in U.S. patent application Ser. No. 14/280,170 entitled "COMPOSITIONS AND METHODS FOR DELIVERY OF HYDROPHOBIC ACTIVE AGENTS" the entire contents of which are herein incorporated by reference.

In some modes of practice, macrolide particulates that are transferred can adhere to the arterial tissue at the target site. Accordingly, the macrolide particulates can release macrolide therapeutic at the target site, which can have a therapeutic effect on the tissue. The macrolide therapeutic at the target site can be useful to control tissue response after balloon dilation. For example, the macrolide particulates can release sirolimus that can inhibit neointimal proliferation at the dilated site.

In some modes of treatment, macrolide particulates can be used to deliver the macrolide therapeutic at a target site in a sustained profile. The particulates including macrolide in crystalline form can more slowly release the macrolide in an amorphous form. In some modes of treatment, the macrolide can be released from the particulate over a desired period of time. For example, the macrolide particulate, by itself, or optionally associated with excipient material such as a polymeric shell around the particulate, or in association with a medical device, can be released in the body over the course of days, weeks, or even months. Release parameters can be determined by various factors, including properties of the particulates, loading of the particulates in a composition or device, and material of the composition or device, such as optional polymeric material associated with the device.

Macrolide therapeutic released from the particulates can be used to treat specific diseases. For example, non-antibiotic macrolide particles can be used in various medical methods such as providing immunosuppressant activity to prevent rejection in organ transplantation. Non-antibiotic macrolides, such as rapamycin, can also be used to prevent hyperplasia and restenosis otherwise associated with inflammation, fibrosis, and thrombosis in tissues responses.

Antibiotic macrolide particles can be used to treat bacterial infections. For example, treatment can be carried out to reduce infection caused by gram-positive bacteria such as *Streptococcus pneumoniae* and *Haemophilus influenzae*, which may soft-tissue and the respiratory tract. Antibiotic macrolides can be used to treat infections caused by organisms such as *Chlamydia*, enterococci, *Legionella pneumophila*, mycoplasma, mycobacteria, rickettsia, pneumococci, streptococci, and staphylococci.

The source of all reagents not specified are available from Sigma-Aldrich, St. Louis, Mo.

EXAMPLE 1

Figure 3:
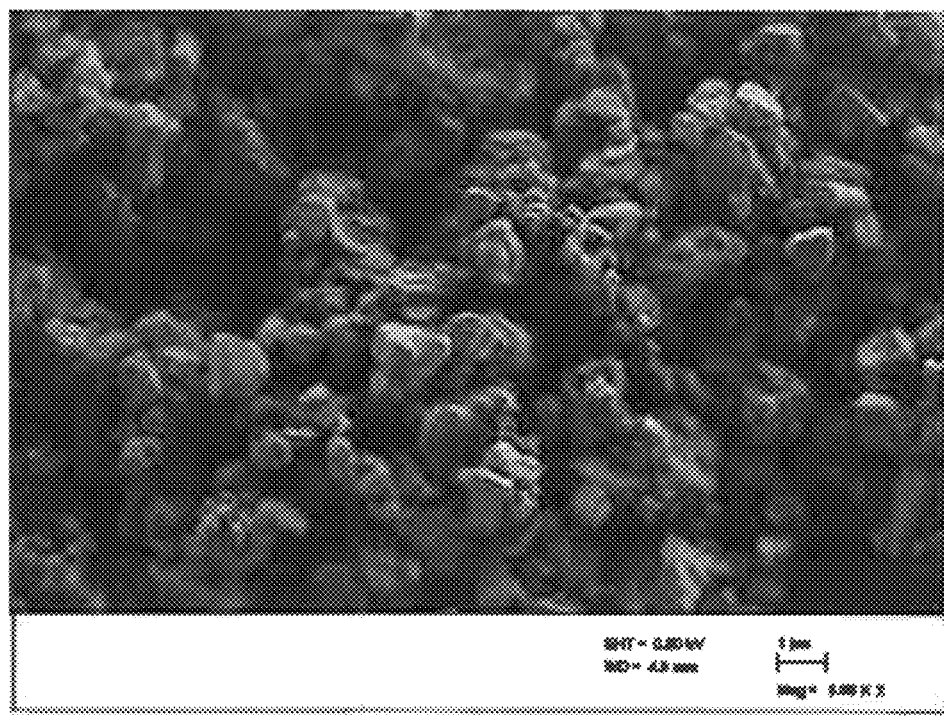
FIG. 3 is an electron micrograph of rapamycin particulates having mean size of approximately 1.5 μm and prepared using a method of the disclosure (Example 1).
Figure 4:
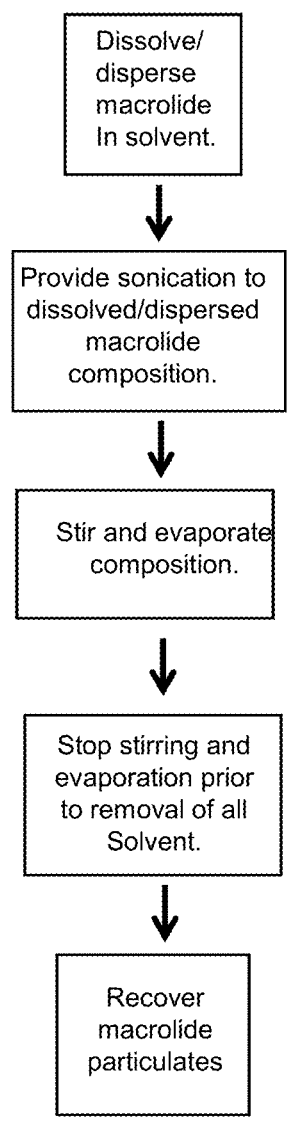
FIG. 4 is a process flow chart including steps for forming rapamycin particulates.

Preparation of Crystalline Sirolimus with an Average Particle Size of Less than 10 μm Sirolimus (100 mg; available from LC Labs, Woburn, Mass.) was added to o-xylene (500 μL) and the mixture was sonicated with a probe sonicator (two times at 2.5 setting for 15 seconds each time; Virsonic™, available from SP Scientific, Warminster, Pa.). The mixture was stirred for 24 hours in an open vessel, allowing the solvent to evaporate, leaving approximately 100 μL at ambient temperature (~25° C.). Stirring was discontinued and the remaining solvent was evaporated in air. The resulting cake was dried at ambient temperature (~25° C.), under vacuum for 2 hours. (FIG. 3)

EXAMPLES 2-6

Preparation of Crystalline Sirolimus; Air Evaporation

Sirolimus (50 mg; available from LC Labs, Woburn, Mass.) containing 0.5% w/w BHT was added to o-xylene (250 μL) in different 1 mL HPLC amber vials to produce slurries with partially dissolved rapamycin. Various solvents were slowly added (Table 3) to the mixtures while being stirred at room temperature until all the solids had dissolved. The solutions were left to evaporate at room-temperature for 3 days until dryness. The resulting cake was further dried at ambient temperature (~25° C.), under vacuum for 2 hours.

A small portion of the samples was dispersed in 1 mL of deionized water by probe-sonication and analyzed for particle size by laser diffraction (CUVETTE, Sympatec). Drops of the dispersions were dried on glass microscope slides and imaged by SEM (FIGS. 7-11). Volume distribution graphs are shown in FIGS. 12-16.

TABLE 2

| Sample | Rapamycin (mg) in 250 μL o-xylene | Solvent | Amount of solvent added μL | Solvent ratio % v/v (o-xylene: solvent) |
| --- | --- | --- | --- | --- |
| 1 | 49.9 | Methanol | 70 | 78:22 |
| 2 | 44.8 | Acetone | 180 | 58:42 |
| 3 | 46.6 | Ethanol | 60 | 81:19 |
| 4 | 48.0 | Acetonitrile | 90 | 74:26 |
| 5 | 47.1 | IPA | 100 | 71:29 |

TABLE 3

| sample | $x_{50}$ (μm) | $x_{90}$ (μm) | $x_{99}$ (μm) | mode (μm) |
| --- | --- | --- | --- | --- |
| methanol | 1.58 ± 0.01 | 6.65 ± 0.17 | 27.27 ± 0.48 | 1.42 |
| ethanol | 1.78 ± 0.01 | 3.75 ± 0.04 | 20.41 ± 0.53 | 1.69 |
| IPA | 1.70 ± 0.01 | 7.43 ± 0.16 | 28.41 ± 0.50 | 1.42 |
| acetone | 1.90 ± 0.08 | 8.37 ± 2.00 | 28.94 ± 0.22 | 1.99 |
| acetonitrile | 1.90 ± 0.01 | 7.73 ± 0.29 | 32.85 ± 1.06 | 1.69 |

EXAMPLE 7

Sirolimus (50 mg; available from LC Labs, Woburn, Mass.) was dissolved in a mixture of o-xylene (250 μL) and ethanol (60 μL) in 1 mL amber vials. 2.5 μL of a BHT solution in o-xylene at 100 mg/mL was added to each of the vials. While stirring at room temperature over night the solvents were evaporated as a stream of nitrogen gas was passed into the reaction vessel through glass pipette, placed at 0 cm, 0.5 cm or 2 cm above the surface of the solution.

Figure 18:
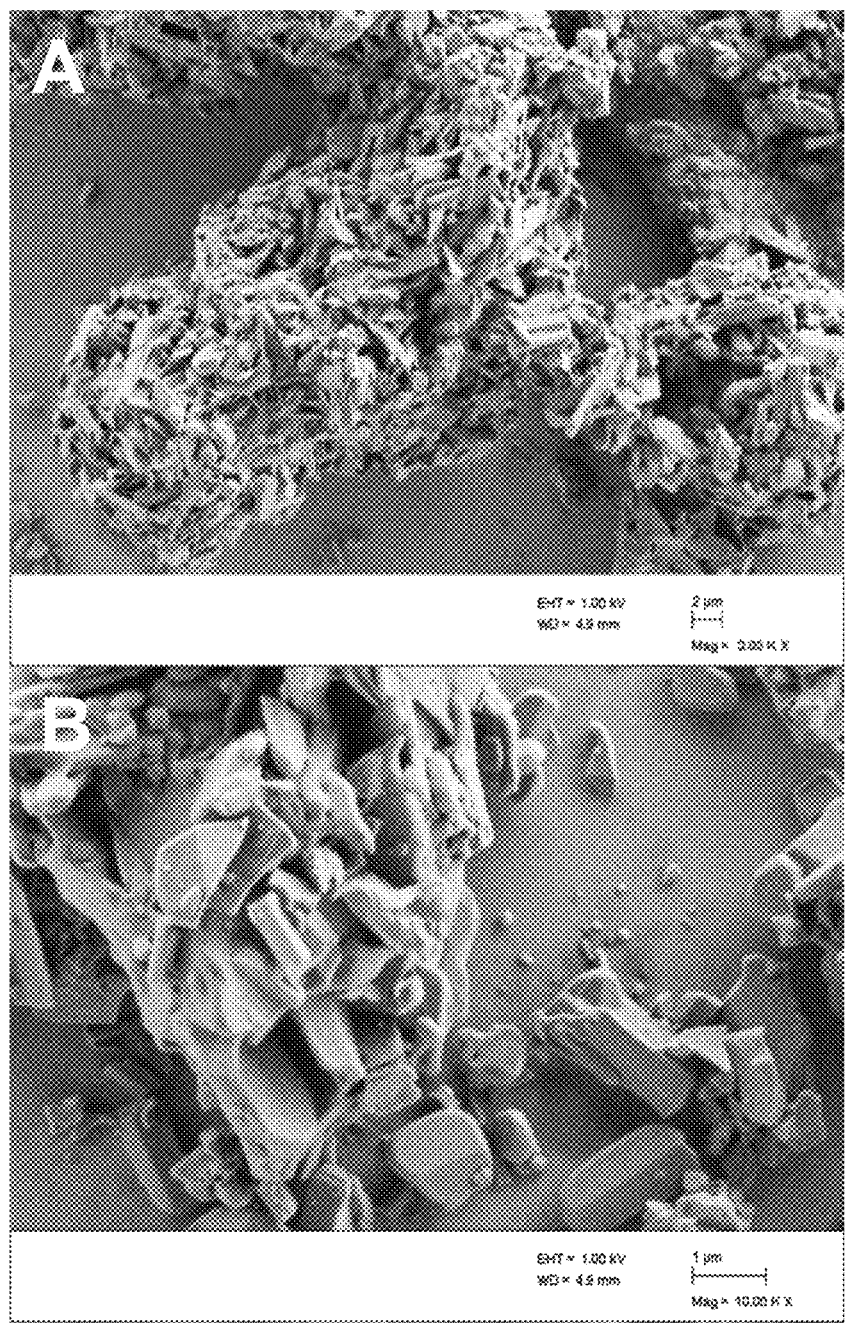
FIGS. 18A (2.00 K× magnification) and B (10.00 K× magnification) are electron micrographs is an electron micrograph, and FIG. 21 a size distribution histogram generated by laser light scattering analysis, of rapamycin crystalline particulates obtained using a mixture of o-xylene and ethanol, and evaporation using a stream of nitrogen at 0 cm from the solvent surface.
Figure 19:
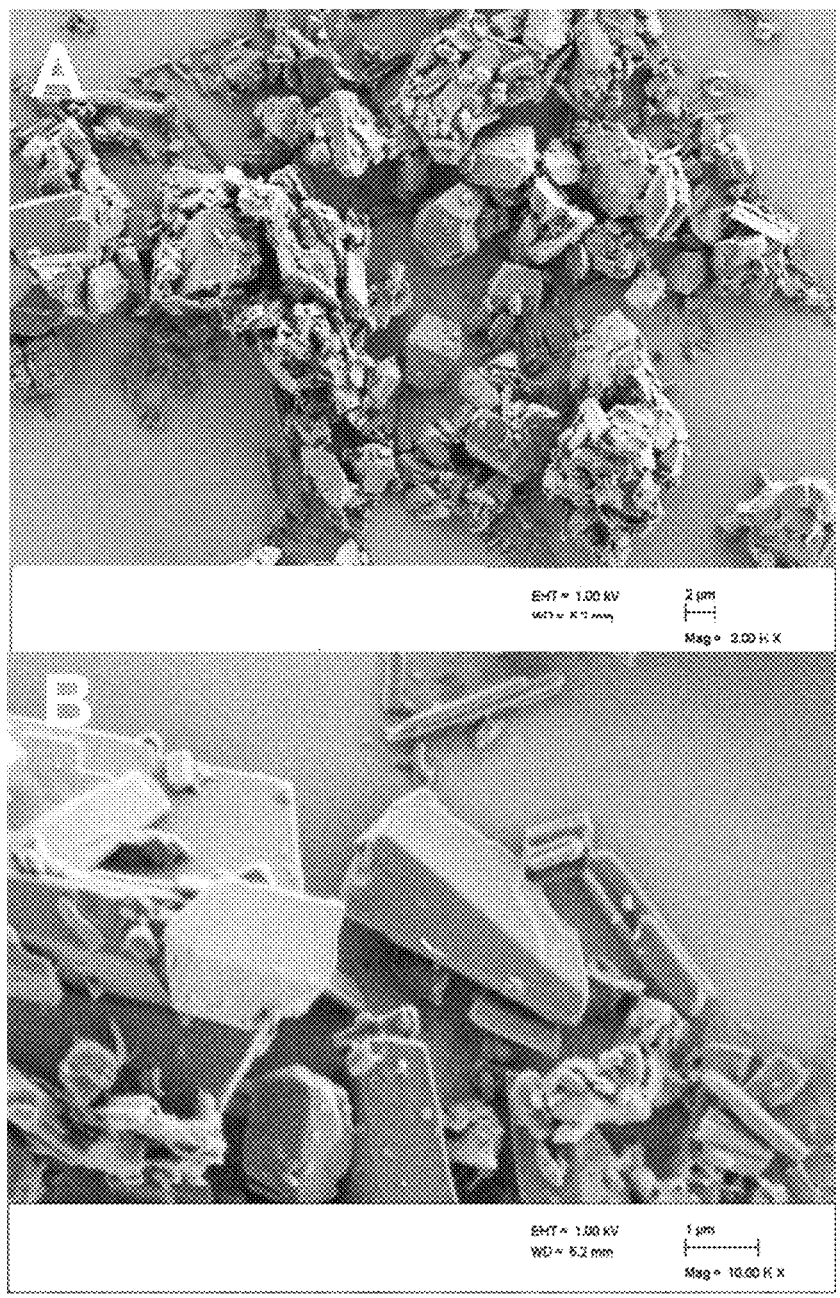
FIGS. 19A (2.00 K× magnification) and B (10.00 K× magnification) are electron micrographs is an electron micrograph, and FIG. 22 a size distribution histogram generated by laser light scattering analysis, of rapamycin crystalline particulates obtained using a mixture of o-xylene and ethanol, and evaporation using a stream of nitrogen at 0.5 cm from the solvent surface.
Figure 20:
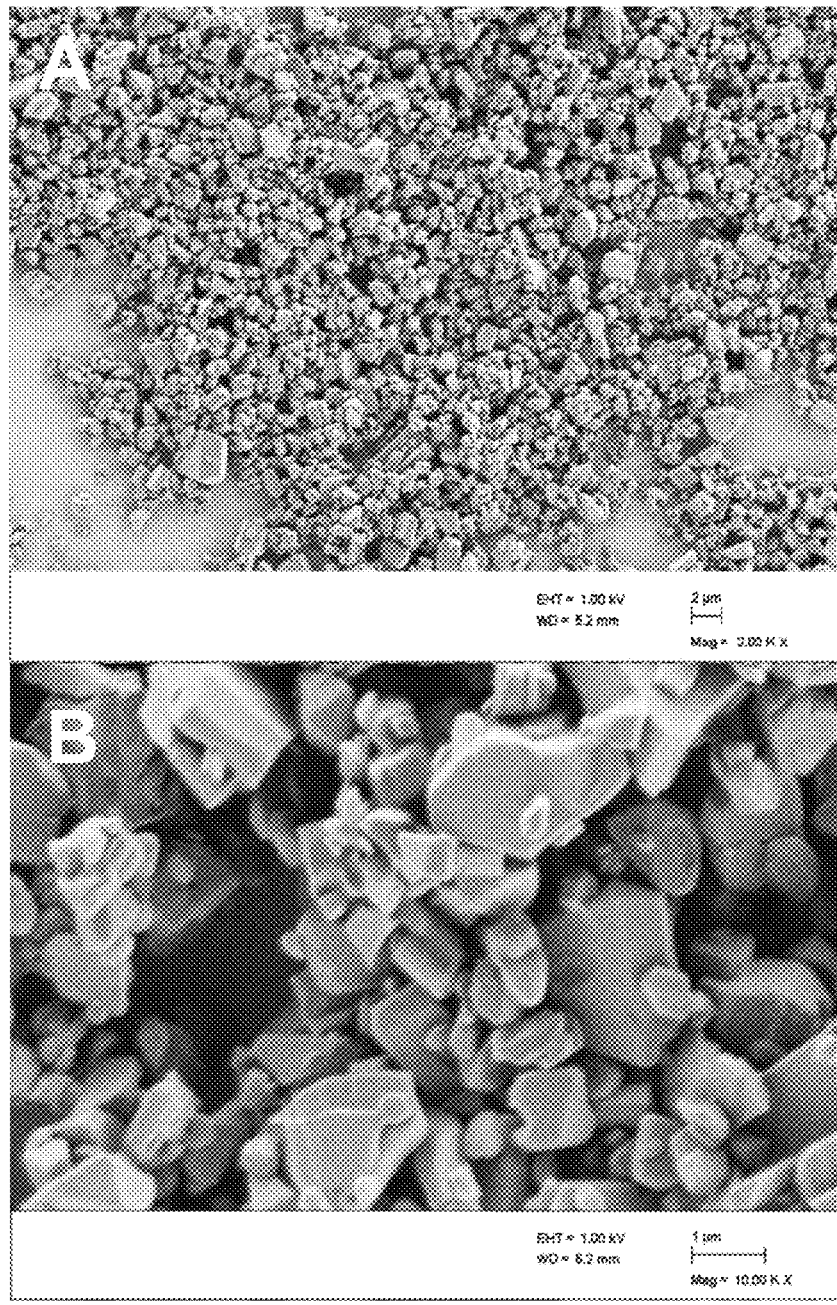
FIGS. 20A (2.00 K× magnification) and B (10.00 K× magnification) are electron micrographs is an electron micrograph, and FIG. 23 a size distribution histogram generated by laser light scattering analysis, of rapamycin crystalline particulates obtained using a mixture of o-xylene and ethanol, and evaporation using a stream of nitrogen at 2.5 cm from the solvent surface.
Figure 21:
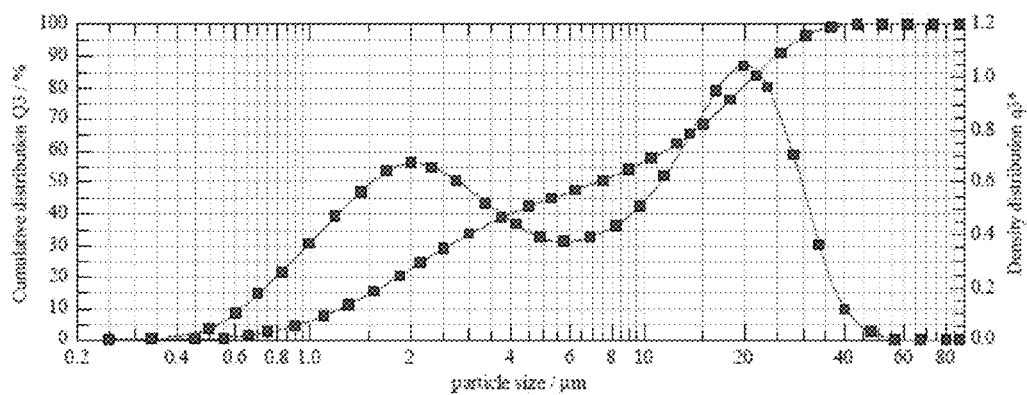
FIGS. 21-23 are particle size distribution histograms corresponding to the particles shown in FIGS. 18-20, respectively.
Figure 22:
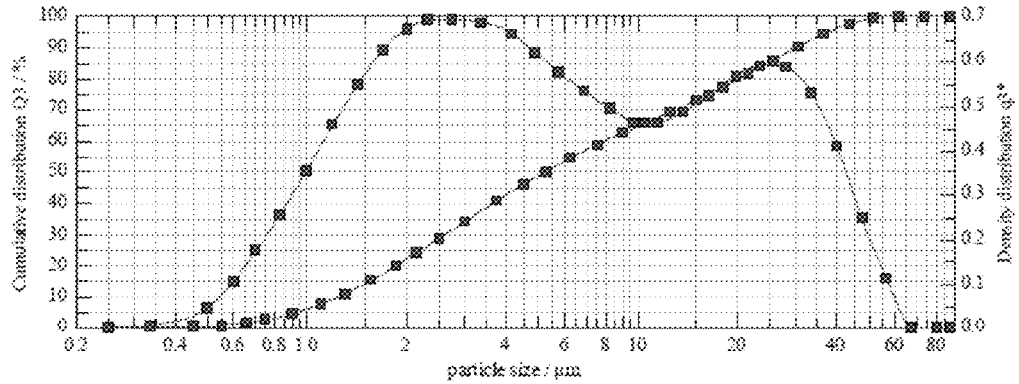
Figure 23:
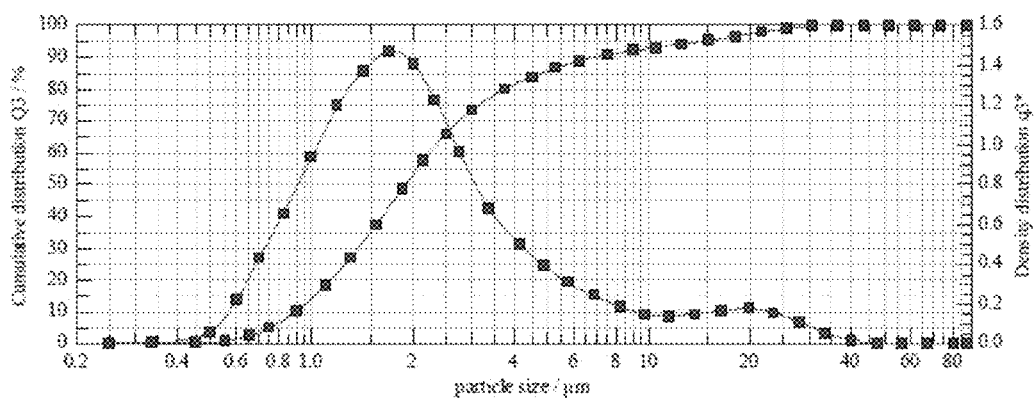

A small portion of the samples was dispersed in 1 mL of deionized water by probe-sonication and analyzed for particle size by laser diffraction (CUVETTE, Sympatec). Drop of the dispersions were dried on glass microscope slides and imaged by SEM and (FIGS. 18-20). Volume distribution graphs are shown in FIGS. 21-23.

TABLE 4

| sample | $x_{50}$ (μm) | $x_{90}$ (μm) | $x_{99}$ (μm) | mode (μm) |
| --- | --- | --- | --- | --- |
| 2.5 cm | 1.91 ± 0.006 | 7.15 ± 0.154 | 27.33 ± 0.725 | 1.69 |
| 0.5 cm | 5.24 ± 0.032 | 30.12 ± 0.188 | 50.66 ± 0.139 | 2.74 and 23.41 |
| 0 cm | 7.45 ± 0.108 | 25.35 ± 0.213 | 38.29 ± 1.083 | 1.99 and 19.67 |

EXAMPLE 8

Sirolimus (500 mg; available from LC Labs, Woburn, Mass.) was dissolved in a mixture of o-xylene (5 mL) and ethanol (1.2 mL). 25 μL of a BHT solution in o-xylene at 100 mg/mL was added. While stirring at room temperature over night the solvents were evaporated as a stream of nitrogen gas was passed into the reaction vessel at about 1 SCFH through glass pipette, placed 2 cm above the surface of the solution. The resulting sirolimus crystals were further dried in a vacuum oven for 2 hours.

Figure 24:
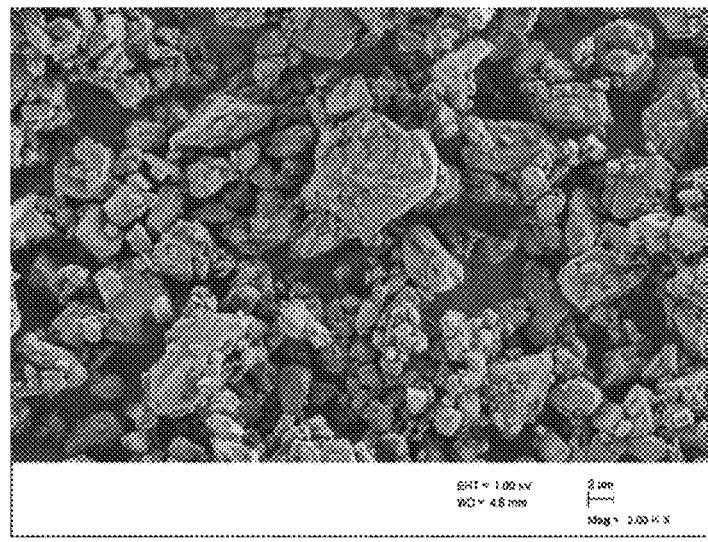
FIG. 24 is an electron micrograph, and FIG. 25 a size distribution histogram generated by laser light scattering analysis, of rapamycin crystalline particulates obtained using a mixture of o-xylene and ethanol, and evaporation using a stream of nitrogen at 2 cm from the solvent surface.
Figure 25:
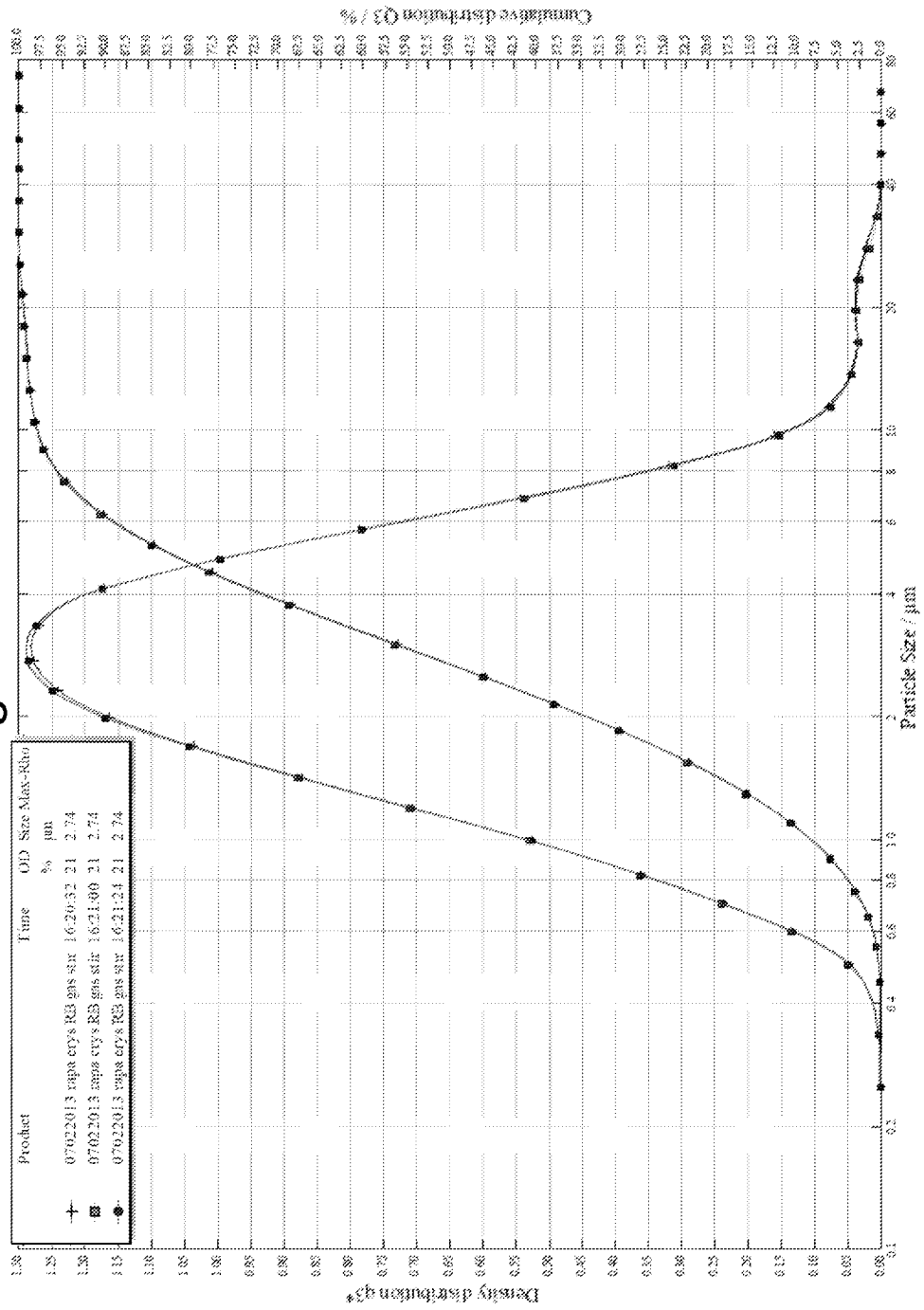

A small portion of the sample was dispersed in 1 mL of deionized water by probe-sonication and analyzed for particle size by laser diffraction (CUVETTE, Sympatec). A drop of the dispersion was dried on a glass microscope slide and imaged by SEM (FIG. 24). A volume distribution graph is shown in FIG. 25.

What is claimed is:

1. A method for preparing macrolide particulates having a size of 10 μm or less, wherein the macrolide is in crystalline form, comprising steps of:
   (a) dissolving and/or dispersing macrolide in a solvent to form a composition;
   (b) forming a supersaturated composition;
   (c) providing sonication in the composition;
   (d) mechanically stirring and evaporating the composition, wherein the solvent is evaporated from the composition during stirring in an amount sufficient to cause formation of the macrolide particulates in the stirred composition, without evaporating an amount which would otherwise cause substantial dry grinding of the particulates while stirring;
   (e) ceasing mechanical stirring prior to complete evaporation of the solvent from the composition; and
   (f) after step (e), removing remaining solvent from the composition to provide the macrolide particulates.

2. The method of claim 1 where, in step (a), the macrolide is dissolved or dispersed in an amount greater than saturation to form the supersaturated composition.

3. The method of claim 1 wherein the solvent comprises xylene.

4. The method of claim 1 wherein the remaining solvent is removed under vacuum.

5. The method of claim 1 wherein the macrolide is selected from the group consisting of rapamycin, everolimus, pimecrolimus, temsirolimus, fujimycin/tacrolimus, deforolimus, zotarolimus, and biolimus.

6. The method of claim 5 wherein the macrolide is rapamycin.

7. The method of claim 1, which provides a set of macrolide particulates wherein the majority of macrolide particulates have size in the range of 1 μm to 6 μm.

8. A method for preparing macrolide particulates having a size of 10 μm or less, wherein the macrolide is in crystalline form, comprising steps of:
   (a) preparing an organic solvent mixture comprising macrolide, a first solvent, and a second solvent selected from the group consisting of an alcohol, acetone, and acetonitrile, wherein the mixture is characterized as providing a maximum solubility for the macrolide that is greater than a maximum solubility of the macrolide dissolved in either the first or second solvent individually; and
   (b) mechanically stirring and evaporating the organic solvent mixture wherein the mixture is evaporated during stirring in an amount sufficient to cause formation of the macrolide particulates in the stirred mixture, without evaporating an amount which would otherwise cause substantial dry orindino of the particulates while stirring; and
   (c) ceasing mechanical stirring prior to complete evaporation of the mixture to provide the macrolide particulates.

9. The method of claim 8, wherein the first solvent and second solvent are present in a volume ratio in the range of 50:50 to 90:10, respectively.

10. The method of claim 8 wherein step (a) comprises a sub-step (a1) of forming a pre-composition of the first solvent and macrolide wherein the macrolide is present in the pre-composition in an amount greater than its maximum solubility.

11. The method of claim 10 wherein step (a) comprises a sub-step (a2) of adding the second solvent to the pre-composition to completely dissolve the macrolide.

12. The method of claim 8 wherein the first solvent is selected from the group consisting of xylene, benzene, and toluene.

13. The method of claim 8 wherein the second solvent is selected from the group consisting of methanol, ethanol, and isopropanol.

14. The method of claim 8 further comprising step (c) of adding a non-solvent to the macrolide particulates and treating with sonication.

15. The method of claim 14, wherein the non-solvent comprises an excipient that is poly(ethyleneimine).

16. A method for preparing macrolide particulates having a size of 10 μm or less, wherein the macrolide is in crystalline form, comprising steps of:
   (a) preparing an organic solvent mixture comprising macrolide, a first solvent that is aromatic, and a second solvent selected from the group consisting of an alcohol, acetone, and acetonitrile, wherein the composition is characterized as providing a maximum solubility for the macrolide that is greater than a maximum solubility of the macrolide dissolved in either the first or second solvent individually; and
   (b) mechanically stirring and evaporating the organic solvent mixture wherein most of, but not more than 80% of the mixture is evaporated from the composition during stirring; and
   (c) ceasing mechanical stirring to provide the macrolide particulates.

17. The method of claim 1 wherein step (b) macrolide is present in the supersaturated composition up to 25% more than a saturation amount in the solvent.

18. The method of claim 1 wherein step (c), step (d), or both steps (c) and (d), are performed at a temperature in the range of 5° C. to 50° C.

19. The method of claim 1 wherein about 99% (wt) or greater of the particulate is macrolide in crystaline form.

20. The method of claim 1 wherein the method provides macrolide particulates having a size in the range of 500 nm to 10 μm.

21. The method of claim 1 wherein the method provides macrolide particulates having a size in the range of 750 nm to 7.5 μm.

22. The method of claim 8 wherein up to about 80% of the mixture is evaporated from the mixture during stirring.

23. The method of claim 16 wherein up to about 80% of the mixture is evaporated from the mixture during stirring.

* * * * *

UNITED STATES PATENT AND TRADEMARK OFFICE
CERTIFICATE OF CORRECTION

PATENT NO. : 9,770,537 B2  
APPLICATION NO. : 14/303309  
DATED : September 26, 2017  
INVENTOR(S) : Joram Slager, Aleksey V. Kurdyumov and Toni M. Heyer Page 1 of 1

It is certified that error appears in the above-identified patent and that said Letters Patent is hereby corrected as shown below:

In the Claims

Column 23
Claim 8, Line 24 "orindino" should be -- grinding --

Signed and Sealed this
Thirty-first Day of December, 2019

Andrei Iancu
*Director of the United States Patent and Trademark Office*